United States Patent
Engstrom et al.

(10) Patent No.: US 12,171,765 B2
(45) Date of Patent: Dec. 24, 2024

(54) COMBINATION THERAPIES USING PRMT5 INHIBITORS FOR THE TREATMENT OF CANCER

(71) Applicant: Mirati Therapeutics, Inc., San Diego, CA (US)

(72) Inventors: Lars Daniel Engstrom, Carlsbad, CA (US); Peter Olson, San Diego, CA (US); James Gail Christensen, San Diego, CA (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 3 days.

(21) Appl. No.: 17/713,455

(22) Filed: Apr. 5, 2022

(65) Prior Publication Data

US 2022/0331323 A1 Oct. 20, 2022

Related U.S. Application Data

(60) Provisional application No. 63/253,029, filed on Oct. 6, 2021, provisional application No. 63/172,643, filed on Apr. 8, 2021.

(51) Int. Cl.
*A61K 31/519* (2006.01)
*A61K 31/506* (2006.01)
*A61P 35/00* (2006.01)

(52) U.S. Cl.
CPC .......... *A61K 31/519* (2013.01); *A61K 31/506* (2013.01); *A61P 35/00* (2018.01)

(58) Field of Classification Search
None
See application file for complete search history.

(56) References Cited

U.S. PATENT DOCUMENTS

2022/0395508 A1* 12/2022 Bhonde ................. A61K 31/55

FOREIGN PATENT DOCUMENTS

| WO | 2016/145150 A2 | 9/2016 | |
|---|---|---|---|
| WO | 2020/027083 A1 | 2/2020 | |
| WO | WO-2021050915 A1 * | 3/2021 | ............. A61P 35/00 |

OTHER PUBLICATIONS

International Search Report mailed on Jul. 1, 2022, in International Application No. PCT/US2022/023388, filed Apr. 5, 2022, 5 pages.
Written Opinion mailed on Jul. 1, 2022, in International Application No. PCT/US2022/023388, filed Apr. 5, 2022, 9 pages.
Kim et al., "Targeting KRAS(G12C): From Inhibitory Mechanism to Modulation of Antitumor Effects in Patients", Cell, 2020, vol. 183, 850-859.
Kryukov et al., "MTAP deletion confers enhanced dependency on the PRMT5 arginine methyltransferase in cancer cells", Science, 2016, 351(6278), 1214-1217.
Abuhammad et al., "Inhibition of the protein arginine methyltransferase PRMT5 overcomes resistance to CDK4-inhibition in melanoma", Pigment Cell & Melanoma Research, 2017, 31(1), 125-230.
Abuhammad et al., "Regulation of PRMT5-MDM4 axis is critical in the response to CDK4/6 inhibitors in melanoma", PNAS, 2019, 116(36), 13 pages.
Shifteh et al., "Protein Arginine Methyltransferase 5 as a Therapeutic Target for KRAS Mutated Colorectal Cancer", Cancers, 2020, vol. 12, 17 pages.

* cited by examiner

*Primary Examiner* — Jeffrey S Lundgren
*Assistant Examiner* — Eric Tran
(74) *Attorney, Agent, or Firm* — Roy Issac

(57) ABSTRACT

This disclosure relates to methods of treating cancer. This disclosure further relates to treating cancer in a subject with compounds that are inhibitors of PRMT5, particularly in combination with CDK4/6 inhibitors.

18 Claims, 5 Drawing Sheets

COMBINATION THERAPIES USING PRMT5 INHIBITORS FOR THE TREATMENT OF CANCER

CROSS-REFERENCE TO RELATED APPLICATIONS

This application claims priority from U.S. Provisional Application No. 63/172,643, filed Apr. 8, 2021, and U.S. Provisional Application No. 63/253,029, filed Oct. 6, 2021, the disclosure of each of which is hereby incorporated by reference in its entirety.

BACKGROUND OF THE DISCLOSURE

Field of the Disclosure

This disclosure relates to methods of treating cancer. This disclosure further relates to treating cancer in a subject with compounds that are inhibitors of protein arginine N-methyl transferase 5 (PRMT5), particularly in combination with cyclin-dependent kinase 4 and 6 (CDK4/6) inhibitors.

Description of Related Art

PRMT5 is a type II arginine methyltransferase that catalyzes the transfer of a methyl group from S-adenosyl-L-methionine (SAM) to an omega-nitrogen of the guanidino function of protein L-arginine residues (omega-monomethylation) and the transfer of a second methyl group to the other omega-nitrogen, yielding symmetric dimethylarginine (sDMA). PRMT5 forms a complex with methylosome protein 50 (MEP50), which is required for substrate recognition and orientation and is also required for PRMT5-catalyzed histone 2A and histone 4 methyltransferase activity (e.g., see Ho et al. (2013) *PLoS ONE* 8(2): e57008).

Homozygous deletions of p16/CDKN2a are prevalent in cancer and these mutations commonly involve the co-deletion of adjacent genes, including the gene encoding methylthioadenosine phosphorylase (MTAP). It is estimated that approximately 15% of all human cancers have a homozygous deletion of the MTAP gene (e.g., see Firestone & Schramm (2017) *J. Am. Chem Soc.* 139(39):13754-13760).

Cells lacking MTAP activity have elevated levels of the MTAP substrate, methylthioadenosine (MTA), which is a potent inhibitor of PRMT5. Inhibition of PRMT5 activity results in reduced methylation activity and increased sensitivity of cellular proliferation to PRMT5 depletion or loss of activity. Hence, the loss of MTAP activity reduces methylation activity of PRMT5 making the cells selectively dependent on PRMT5 activity.

Despite importance of PRMT5 on cell viability and its prevalence in cancers, effective therapies that inhibit PRMT5 have been elusive. Thus, there remains a need to develop new PRMT5 inhibitor therapies to treat wide range of cancers.

SUMMARY OF THE DISCLOSURE

One aspect of the disclosure provides methods for treating cancer in a subject. Such methods include administering to the subject a therapeutically effective amount of a CDK4/6 inhibitor and a therapeutically effective amount of a PRMT5 inhibitor.

Also provided herein is a method for treating cancer in a subject in need thereof. Such methods include determining that the cancer is associated with MTAP homozygous deletion (e.g., an MTAP-associated cancer). These methods optionally further include determining that the cancer is associated with a CDKN2A homozygous deletion. Such methods further include administering to the subject a therapeutically effective amount of a CDK4/6 inhibitor and a therapeutically effective amount of a PRMT5 inhibitor.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The accompanying drawings are included to provide a further understanding of the methods of the disclosure, and are incorporated in and constitute a part of this specification. The drawings illustrate one or more embodiment(s) of the disclosure and, together with the description, serve to explain the principles and operation of the disclosure.

DETAILED DESCRIPTION OF THE DISCLOSURE

Figure 1:
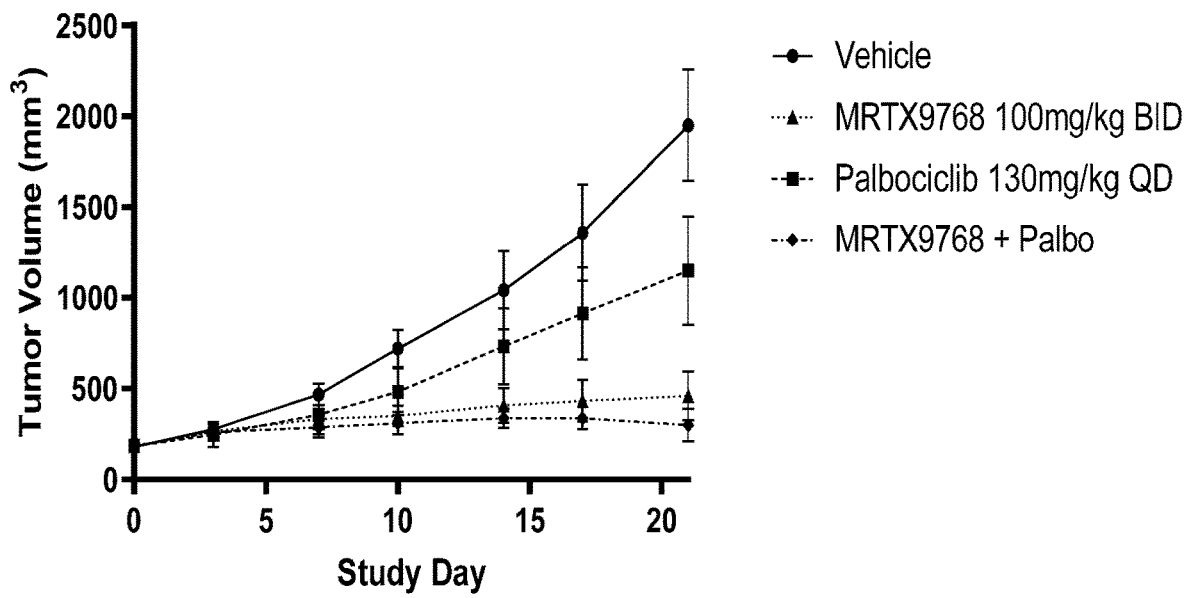
FIG. 1 illustrates the results of the methods of Example 1 in the $KRAS^{G12C}$ and $CDKN2A/MTAP^{DEL}$ lung tumor xenograft LU99 model grown in immunodeficient mice. The PRMT5 inhibitor used in this method was MRTX9768 administered at 100 mg/kg twice a day (BID), and the CDK4/6 inhibitor was palbociclib administered at 130 mg/kg once a day (QD). Average tumor volume±standard error is plotted of the mean at study day as indicated.

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. The present disclosure provides improvements in treating cancer in a subject. As used herein, the terms "subject" or "patient" are used interchangeably, refers to any animal, including mammals, and most preferably humans.

The methods provided herein may be used for the treatment of a wide variety of cancer including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiforme, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In certain embodiments of the methods of the disclosure, the cancer is a MTAP-associated cancer. For example, in certain embodiments, the cancer comprises MTAP gene homozygous deletion ($MTAP^{DEL}$). The subject may be identified or diagnosed as having MTAP-associated cancer where, for example, $MTAP^{DEL}$ is determined using a suitable assay or a kit. Alternatively, the subject is suspected of having MTAP-associated cancer or the subject has a clinical record indicating that the subject has MTAP-associated cancer.

In certain embodiments of the methods of the disclosure, the cancer comprises a cyclin-dependent kinase inhibitor 2A (CDKN2A) gene homozygous deletion ($CDKN2A^{DEL}$). The subject may be identified or diagnosed as having $CDKN2A^{DEL}$ where the deletion is determined using a suitable assay or a kit. Alternatively, the subject is suspected of having the $CDKN2A^{DEL}$ cancer, or the subject has a clinical record indicating that the subject has the $CDKN2A^{DEL}$ cancer.

In certain embodiments of the methods of the disclosure, the cancer may further comprise a Kirsten rat sarcoma viral oncogene homolog (KRAS) gene mutation, such as glycine-to-cysteine ($KRAS^{G12C}$) gene mutation. The subject may be identified or diagnosed as having $KRAS^{G12C}$ cancer where $KRAS^{G12C}$ mutation is determined using a suitable assay or a kit. Alternatively, the subject is suspected of having the KRAS$^{G12C}$ cancer or the subject has a clinical record indicating that the subject has the KRAS$^{G12C}$ cancer.

In some embodiments of any of the methods or uses described herein, an assay is used to determine whether the patient has MTAP$^{DEL}$ and/or CDKN2A$^{DEL}$ and/or KRAS$^{G12C}$ using a sample (e.g., a biological sample or a biopsy sample such as a paraffin-embedded biopsy sample) from a subject. Such assay includes, but is not limited to, next generation sequencing, immunohistochemistry, fluorescence microscopy, break apart FISFI analysis, Southern blotting. Western blotting, FACS analysis, Northern blotting, and PCR-based amplification (e.g., RT-PCR and quantitative real-time RT-PCR). As is well known in the art, the assays are typically performed, e.g., with at least one labelled nucleic acid probe or at least one labelled antibody or antigen-binding fragment thereof.

In certain embodiments, the cancer in the methods of the disclosure is selected from lung cancer, pancreatic cancer, head and neck cancer, bladder cancer, esophageal cancer, lymphoma, stomach cancer, skin cancer, breast cancer, brain cancer, liver cancer, and colon cancer.

In certain embodiments, the cancer in the methods of the disclosure is selected from lung cancer, pancreatic cancer, head and neck cancer, bladder cancer, esophageal cancer, lymphoma, stomach cancer, skin cancer, breast cancer, and brain cancer.

In certain embodiments, the cancer in the methods of the disclosure is selected from lung cancer (e.g., mesothelioma or non-small cell lung cancer (NSCLC) including adenocarcinoma and squamous cell), pancreatic cancer, head and neck cancer (such as squamous cell carcinoma (HNSCC)), bladder cancer, esophageal cancer, lymphoma (e.g., diffuse large B-cell lymphoma), stomach cancer, melanoma, breast cancer, and brain cancer (e.g., glioblastoma multiforme and glioma).

In certain embodiments, the cancer in the methods of the disclosure is selected from mesothelioma, NSCLC (e.g., adenocarcinoma and squamous cell), pancreatic cancer, HNSCC, and bladder cancer.

In one embodiment of the methods of the disclosure, the cancer is lung cancer. For example, the lung cancer may be NSCLC (e.g., adenocarcinoma and squamous cell) or mesothelioma.

In one embodiment of the methods of the disclosure, the cancer is pancreatic cancer. In another embodiment, the cancer is head and neck cancer. In yet another embodiment, the cancer is bladder cancer.

As provided above, the CDK4/6 inhibitor is administered in the methods of the disclosure. As used herein, a "CDK4/6 inhibitor" refers to compounds capable of negatively modulating or inhibiting all or a portion of the enzymatic activity of CDK4/6. The CDK4/6 inhibitors of the present disclosure interact with and/or irreversibly bind to CDK4/6 resulting in the inhibition of the enzymatic activity of CDK4/6 and blocking the transition from the G1 to the S phase of the cell cycle.

In certain embodiments, the CDK4/6 inhibitor also inhibits CDK2, i.e., it is a CDK 2/4/6 inhibitor.

In certain embodiments, the CDK4/6 inhibitor is selected from palbociclib (sold as Ibrance®, Pfizer Inc., New York, New York), abemaciclib (sold as Verzenio®, Eli Lilly and Company, Indianapolis, Ind.), ribociclib (sold as Kisqali®, Novartis Pharmaceuticals, Basel, Switzerland), PF-06873600 (CAS No. 2185857-97-8, available from Pfizer Inc., New York, New York), and combinations thereof. In certain embodiments, the CDK4/6 inhibitor is trilaciclib (sold as Cosela™, G1 Therapeutics, Inc., Durham, North Carolina).

In one embodiment of the methods of the disclosure, the CDK4/6 inhibitor is palbociclib.

As provided above, the PRMT5 inhibitor is also administered in the methods of the disclosure. A "PRMT5 inhibitor" as used herein refers to compounds of the disclosure as described herein. These compounds are capable of negatively modulating or inhibiting all or a portion of the enzymatic activity of the PRMT5, particularly, in the presence of bound MTA in vitro or in vivo or in cells expressing elevated levels of MTA. In certain embodiments, the PRMT5 inhibitor is a MTA-cooperative PRMT5 inhibitor.

In certain embodiments, the PRMT5 inhibitor of the disclosure is any one of the PRMT5 inhibitors disclosed in International patent publication No. WO 2021/050915 A1, published 18 Mar. 2021, incorporated by reference in its entirety.

In certain other embodiments, the PRMT5 inhibitor of the disclosure is any one of the PRMT5 inhibitors disclosed in U.S. provisional application No. 63/200,521, filed 11 Mar. 2021, incorporated by reference in its entirety.

For example, the PRMT5 inhibitor in the methods of the disclosure as described herein is a compound of Formula IIA, IIB or IIC (Embodiment 1):

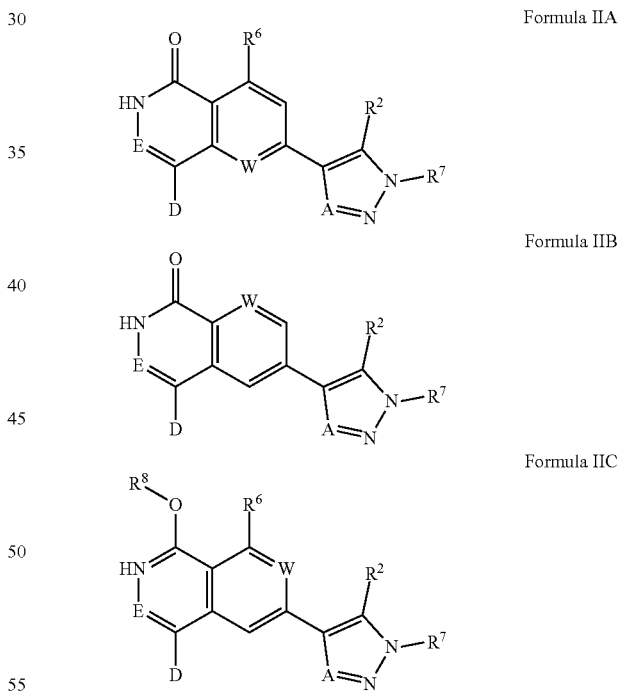

or a pharmaceutically acceptable salt thereof, wherein:

A is CR$^9$ or N;

D is (C(R$^9$)$_2$)$_{1-2}$—NH$_2$,

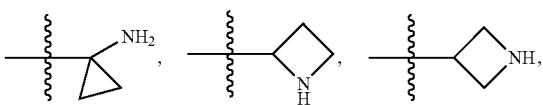

-continued or D is where the methylene is bonded to E where E is C;
E is C, $CR^9$ or N;
each L is independently a bond or $C_1$-$C_3$ alkylene;
W is $CR^9$ or N;
each X is independently a bond, O, S, —$NR^4$— or —$NR^4$C(O)—;
each Z is independently a bond, —SO—, —$SO_2$—, —CH(OH)— or —C(O)—;
each $R^2$ is independently hydroxy, halogen, cyano, cyanomethyl, —$(NR^4)_2$, hydroxyalkyl, alkoxy, —$SO_2C_1$-$C_3$alkyl, —X-ar$C_1$-$C_3$alkyl, heteroalkyl, $C_2$-$C_4$ alkynyl, —X-haloalkyl, —X-$C_1$-$C_5$ alkyl, —Z-$C_1$-$C_5$ alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;
each $R^4$ is independently hydrogen or $C_1$-$C_3$ alkyl;
each $R^5$ is independently cyano, oxo, halogen, $C_1$-$C_3$ alkyl, hydroxyalkyl, hydroxy, alkoxy, alkoxy-$C_1$-$C_3$ alkyl, —X-haloalkyl, —Z-cycloalkyl, —X-ar$C_1$-$C_3$alkyl, —X-ar$C_1$-$C_3$alkyl substituted with cyano, —X-L-cycloalkyl optionally substituted with $C_1$-$C_3$ alkyl or oxo, —X-L-heteroaryl optionally substituted with one or more $C_1$-$C_3$ alkyl or oxo, —X-L-heterocyclyl optionally substituted with one or more $C_1$-$C_3$ alkyl or oxo, or —X-aryl;
$R^6$ is hydrogen, halogen, $C_1$-$C_3$ alkyl, haloalkyl, hydroxy, alkoxy, $C_1$-$C_3$ alkyl-alkoxy, $N(R^9)_2$, $NR^9C(O)R^9$, $C(O)R^9$, oxetane and THF;
$R^7$ is H or $C_1$-$C_3$ alkyl optionally substituted with one or more halogen;
$R^8$ is H or $C_1$-$C_3$ alkyl; and
each $R^9$ is independently H or $C_1$-$C_3$ alkyl, halogen or haloalkyl.

Embodiment 2 provides the PRMT5 inhibitor in the methods of the disclosure as a compound of Formula IIA:

Formula IIA

Embodiment 3 provides the PRMT5 inhibitor in the methods of the disclosure as a compound of Formula IIB:

Formula IIB

Embodiment 4 provides the PRMT5 inhibitor in the methods of the disclosure as a compound of Formula IIC:

Formula IIC

Embodiment 5 provides the method of any of embodiments 1-4, wherein W is $CR^9$.

Embodiment 6 provides the method of any of embodiments 1-4, wherein A is $CR^9$.

Embodiment 7 provides the method of any of embodiments 1-4, wherein E is N.

Embodiment 8 provides the method of any of embodiments 1-7, wherein W is $CR^9$, A is $CR^9$ and E is N.

Embodiment 9 provides the method of any of embodiments 1-8, wherein $R^2$ is selected from: benzothiophene, naphthalene, quinoline, chromane, isochromane, dihydrobenzodioxine, indolazine, tetrahydroindolazine, dihydroisobenzofuran, benzene, isoquinolinone, benzodioxone, thienopyridine, tetrahydroindolone, indolizine, dihydroindolizinone, imadazopyridinone, thienopyrimidine, thiophene, pyrrolopyrimidinone, thiazolopyridinone, dihydropyrrolizine, isoindalone and tetrahydroisoquinoline.

Embodiment 10 provides the method of any of embodiments 1-8, wherein each $R^5$ is independently cyano, oxo, halogen, C1-C3 alkyl, hydroxy, hydroxyalkyl, alkoxy-C1-C3alkyl, —X-L-heterocyclyl optionally substituted with one or more C1-C3alkyl or oxo, —X-L-cycloalkyl optionally substituted with C1-C3 alkyl or oxo.

Embodiment 11 provides the method of any of embodiments 1-8, wherein $R^6$ is selected from hydrogen, hydroxy, chlorine, —NHC(O)$CH_3$, —C(O)$CF_2$H, —$NH_2$, —$CF_2$, —$CH_3$, —O—$CH_2CH_3$, —$CH_2$—$CH_2$—O—$CH_3$, oxetane and THF.

Embodiment 12 provides the method of any of embodiments 1-11, where one of L, X and Z is a bond.

Embodiment 13 provides the method of embodiment 12, wherein all of L, X and Z are bonds.

One aspect of the disclosure provides the method wherein the PRMT5 inhibitor is a compound of the formula (IIIC) (Embodiment 14):

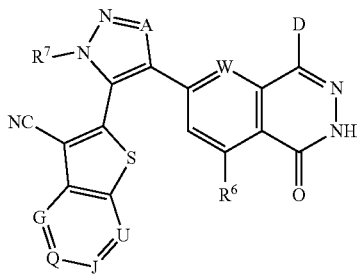

(IIIC)

or a pharmaceutically acceptable salt thereof, wherein
A is $CR^9$ or N;
D is —$CH_2$—$NH_2$,

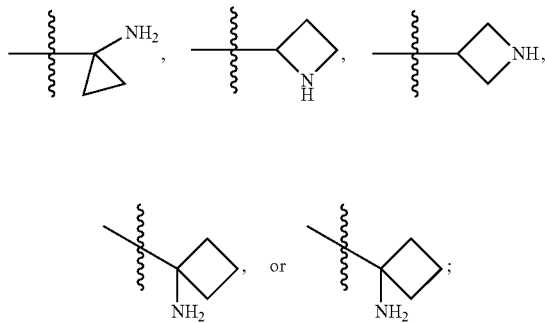

W is $CR^9$ or N, where $R^9$ is H or $C_1$-$C_3$ alkyl;
G, Q, J and U are independently selected from C(H), C($R^5$), and N, provided only one or two of G, Q, J, and U can be N;
each $R^5$ is independently hydroxy, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl;
$R^6$ is hydrogen, halogen, $C_1$-$C_6$ alkyl, $C_1$-$C_6$ haloalkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —$NR^{15}$(CO)$R^{16}$, where each $R^9$ is independently H or $C_1$-$C_3$ alkyl, $R^{15}$ is hydrogen or methyl, and $R^{16}$ is $C_1$-$C_3$ alkyl; and
$R^7$ is $C_1$-$C_3$ alkyl or $C_1$-$C_3$ haloalkyl.

Embodiment 15 provides the method according to embodiment 14, wherein A is CH.

Embodiment 16 provides the method according to embodiment 14 or 15, wherein W is N.

Embodiment 17 provides the method according to embodiment 14 or 15, wherein W is CH.

Embodiment 18 provides the method according to any of embodiments 14-17, wherein D is —$CH_2$—$NH_2$.

Embodiment 19 provides the method of the disclosure wherein the PRMT5 inhibitor is a compound according to embodiment 14 of the formula:

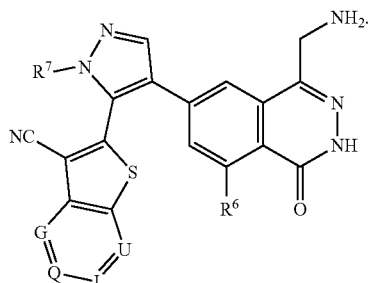

Embodiment 20 provides the method according to any of embodiments 14-19, wherein $R^6$ is hydrogen, halogen, $C_1$-$C_6$ alkyl, $C_1$-$C_6$ haloalkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —$NR^{15}$(CO)$R^{16}$.

Embodiment 21 provides the method according to any of embodiments 14-19, wherein $R^6$ is hydrogen, halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —$NR^{15}$(CO)$R^{16}$.

Embodiment 22 provides the method according to any of embodiments 14-19, wherein $R^6$ is hydrogen, chloro, fluoro, methyl, ethyl, difluoromethyl, hydroxy, methoxy, ethoxy, (methoxy) methyl, (ethoxy) methyl, (methoxy) ethyl, (ethoxy)ethyl, oxetanyl, tetrahydrofuranyl, —C(O)-difluoromethyl, —$NH_2$, or —NH(CO)$CH_3$.

Embodiment 23 provides the method according to any of embodiments 14-19, wherein $R^6$ is halogen, $C_1$-$C_6$ alkyl, $C_1$-$C_6$ haloalkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —$NR^{15}$(CO)$R^{16}$.

Embodiment 24 provides the method according to any of embodiments 14-19, wherein $R^6$ is halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —$NR^{15}$(CO)$R^{16}$.

Embodiment 25 provides the method according to any of embodiments 14-19, wherein $R^6$ is chloro, fluoro, methyl, ethyl, difluoromethyl, hydroxy, methoxy, ethoxy, (methoxy) methyl, (ethoxy) methyl, (methoxy)ethyl, (ethoxy)ethyl, oxetanyl, tetrahydrofuranyl, —C(O)-difluoromethyl, —$NH_2$, or —NH(CO)$CH_3$.

Embodiment 26 provides the method according to any of embodiments 23-25, wherein each G, Q, J and U is independently C(H).

Embodiment 27 provides the method according to any of embodiments 23-25, wherein G, Q, J and U are independently selected from C(H) and C($R^5$).

Embodiment 28 provides the method according to any of embodiments 23-25, wherein G, Q, J and U are independently selected from C(H) and N.

Embodiment 29 provides the method according to any of embodiments 14-19, wherein
$R^6$ is hydrogen;
at least one of G, Q, J, and U is C($R^5$), and the remaining G, Q, J, and U are independently selected from C(H), C($R^5$) and N, wherein each $R^5$ is independently hydroxy, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl.

Embodiment 30 provides the method according to embodiment 29, wherein one or two of G, Q, J and U is N.

Embodiment 31 provides the method according to any of embodiments 14-19, wherein $R^6$ is hydrogen;

at least one of G, Q, J, and U is $C(R^5)$, and the remaining G, Q, J, and U are independently selected from C(H) and $C(R^5)$, wherein each $R^5$ is independently hydroxy, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl.

Embodiment 32 provides the method according to embodiment 31, wherein at least one of G, Q, J, and U is $C(R^5)$, and the remaining G, Q, J, and U are independently C(H); for example only one of G, Q, J, and U is $C(R^5)$.

Embodiment 33 provides the method according to embodiment 31, wherein two of G, Q, J, and U is $C(R^5)$, and the remaining G, Q, J, and U are independently C(H).

Embodiment 34 provides the method according to embodiment 31, wherein three of G, Q, J, and U is $C(R^5)$, and the remaining G, Q, J, and U is C(H).

Embodiment 35 provides the method according to any of embodiments 14-19, wherein G, Q, J, and U together with the thiophene to which they are attached form:

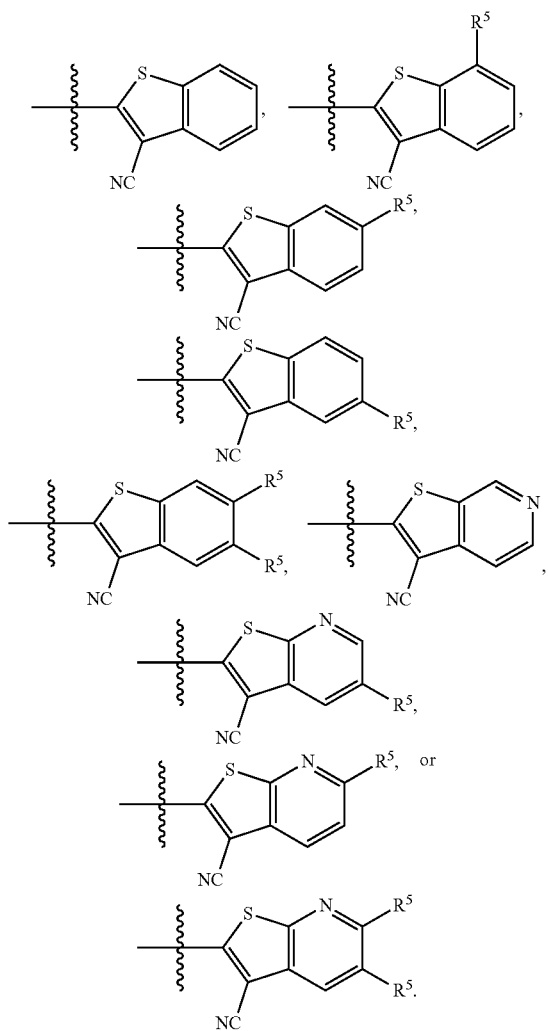

Embodiment 36 provides the method according to embodiment 35, wherein G, Q, J, and U together with the thiophene ring to which they are attached form a benzo[b]thiophene.

Embodiment 37 provides the method according to any one of embodiments 14-36, wherein $R^5$, if present, is hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl.

Embodiment 38 provides the method according to any one of embodiments 14-36, wherein $R^5$, if present, is hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ heterocycloalkyl, or $C_1$-$C_3$ alkoxy$C_1$-$C_3$ alkyl.

Embodiment 39 provides the method according to any one of embodiments 14-36, wherein $R^5$, if present, is hydroxy, chloro, fluoro, methyl, ethyl, methoxy, ethoxy, 2,2-difluoroethoxy, oxetanyl, tetrahydrofuranyl, (methoxy)methyl, (ethoxy)methyl, (methoxy)ethyl, or (ethoxy)ethyl.

Embodiment 40 provides the method according to any one of embodiments 14-39, wherein $R^7$ is methyl.

Embodiment 41 provides the method according to any one of embodiments 14-39, wherein $R^7$ is ethyl.

Embodiment 42 provides the method according to any one of embodiments 14-39, wherein $R^7$ is propyl (e.g., isopropyl).

Embodiment 43 provides the method according to any one of embodiments 14-39, wherein $R^7$ is difluoromethyl or trifluoromethyl.

Embodiment 44 provides the method according to embodiment 14, wherein the PRMT5 inhibitor is of the formula:

wherein

G, Q, J, and U together with the thiophene to which they are attached form:

-continued

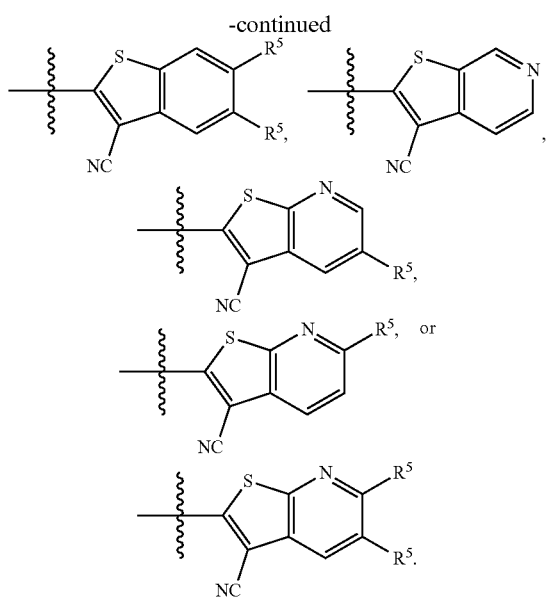

where each $R^5$ is independently hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ heterocycloalkyl, or $C_1$-$C_3$ alkoxy$C_1$-$C_3$ alkyl; and $R^6$ is hydrogen, halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —NR$^{15}$(CO)R$^{16}$.

Embodiment 45 provides the method according to embodiment 14, wherein the PRMT5 inhibitor is of the formula:

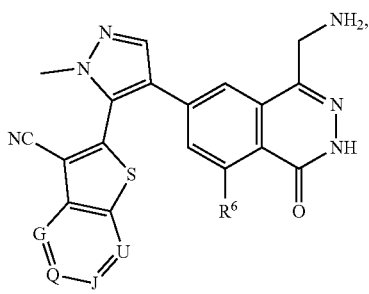

wherein

G, Q, J, and U together with the thiophene to which they are attached form:

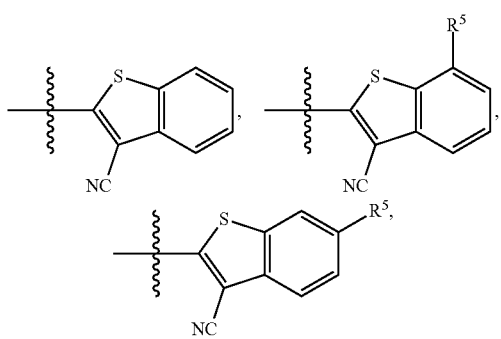

-continued

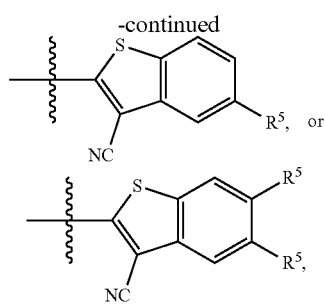

where each $R^5$ is independently hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ heterocycloalkyl, or $C_1$-$C_3$ alkoxy$C_1$-$C_3$ alkyl; and $R^6$ is halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —NR$^{15}$(CO)R$^{16}$.

Embodiment 46 provides the method according to embodiment 14, wherein the PRMT5 inhibitor is of the formula:

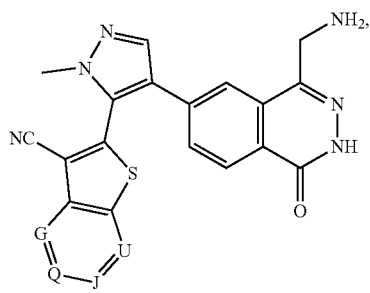

wherein

G, Q, J, and U together with the thiophene to which they are attached form:

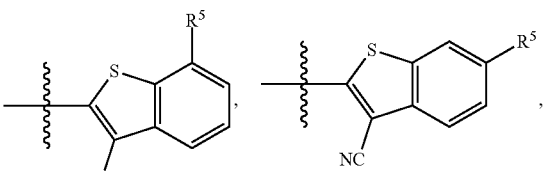

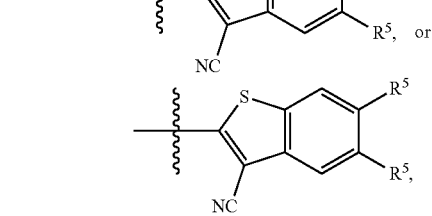

where each $R^5$ is independently hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ heterocycloalkyl, or $C_1$-$C_3$ alkoxy$C_1$-$C_3$ alkyl.

Embodiment 47 provides the method of the disclosure wherein the PRMT5 inhibotor is a compound of the formula (IIIB):

(IIIB)

or a pharmaceutically acceptable salt thereof, wherein
A is $CR^9$ or N;
D is —$CH_2$—$NH_2$, W is $CR^9$ or N, where $R^9$ is H or $C_1$-$C_3$ alkyl;
$R^{51}$ is hydrogen, fluoro, chloro, or methyl, or $R^{51}$ and $R^{52}$ together with atoms to which they are attached form a $C_4$-$C_6$ heterocycloalkyl (e.g, hydrofuranyl);
$R^{52}$ is fluoro, chloro, or methyl, or $R^{52}$ and $R^{53}$ together with atoms to which they are attached form a phenyl;
$R^{53}$ is hydrogen, fluoro, chloro, or methyl;
$R^{54}$ is hydrogen, halogen, $C_1$-$C_3$ alkyl, or $C_1$-$C_3$ alkoxy;
$L^5$ is —O— or —$CH_2$—;
$R^6$ is hydrogen, halogen, $C_1$-$C_6$ alkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, or —$NR^{15}(CO)R^{16}$, where $R^{15}$ is hydrogen or methyl, and $R^{16}$ is $C_1$-$C_3$ alkyl;
$R^7$ is $C_1$-$C_3$ alkyl or $C_1$-$C_3$ haloalkyl.

Embodiment 48 provides the method according to embodiment 47, wherein:
A is —CH or —$CCH_3$;
D is —$CH_2$—$NH_2$;
W is —CH, —$CCH_3$, or N;
$R^{51}$, $R^{52}$, $R^{53}$, and $R^{54}$ are each independently selected from hydrogen, fluoro, chloro, or methyl;
$L^5$ is —O—;
$R^6$ is hydrogen, fluoro, chloro, or methyl; and
$R^7$ is $C_1$-$C_2$ alkyl or $C_1$-$C_2$ haloalkyl.

Embodiment 49 provides the method according to embodiment 47 or embodiment 48, wherein:
A and W are —CH;
D is —$CH_2$—$NH_2$;
$R^{51}$, $R^{52}$, and $R^{53}$ are each independently selected from hydrogen, fluoro, chloro, and methyl;
$R^{54}$ is hydrogen;
$L^5$ is —O—;
$R^6$ is hydrogen; and
$R^7$ is methyl.

Embodiment 50 provides the method according to any of embodiments 47-49, wherein:
A and W are —CH;
D is —$CH_2$—$NH_2$;
$R^{51}$ and $R^{52}$ are each independently selected from fluoro, chloro, and methyl;
$R^{53}$ and $R^{54}$ are hydrogen;
$L^5$ is —O—;
$R^6$ is hydrogen; and
$R^7$ is methyl.

Embodiment 51 provides the method according to embodiment 47, wherein A is CH.

Embodiment 52 provides the method according to embodiment 47 or 48, wherein W is N.

Embodiment 53 provides the method according to embodiment 47 or 48, wherein W is CH.

Embodiment 54 provides the method according to any of embodiments 47-50, wherein D is —$CH_2$—$NH_2$.

Embodiment 55 provides the method according to any of embodiments 47-51, wherein $R^{54}$ is hydrogen or methyl.

Embodiment 56 provides the method according to any of embodiments 47-51, wherein $R^{54}$ is hydrogen.

Embodiment 57 provides the method according to any of embodiments 47-51, wherein $R^{54}$ is methyl.

Embodiment 58 provides the method according to embodiment 47, where the PRMT5 inhibitor is of the formula:

such as e.g.,

Embodiment 59 provides the method according to any of embodiments 47-55, wherein $L^5$ is —$CH_2$—.

Embodiment 60 provides the method according to any of embodiments 47-55, wherein $L^5$ is —O—.

Embodiment 61 provides the method according to any of embodiments 47-57, wherein $R^6$ is hydrogen, halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —$N(R^9)_2$, or —$NR^{15}(CO)R^{16}$; for example, wherein $R^6$ is hydrogen, chloro, fluoro, methyl, ethyl, difluoromethyl, hydroxy, methoxy, ethoxy, (methoxy)methyl, (ethoxy) methyl, (methoxy)ethyl, (ethoxy)ethyl, oxetanyl, tetrahydrofuranyl, —C(O)-difluoromethyl, —$NH_2$, or —NH(CO)$CH_3$.

Embodiment 62 provides the method according to any of embodiments 47-57, wherein $R^6$ is hydrogen, halogen, $C_1$-$C_6$ alkyl, or $C_1$-$C_6$ alkoxy; for example, $R^6$ is hydrogen, halogen, $C_1$-$C_3$ alkyl, or $C_1$-$C_3$ alkoxy.

Embodiment 63 provides the method according to any of embodiments 47-57, wherein $R^6$ is hydrogen, chloro, fluoro, methyl, ethyl, methoxy, or ethoxy.

Embodiment 64 provides the method according to any of embodiments 47-57, wherein $R^6$ is halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —NR$^{15}$(CO)R$^{16}$; for example, wherein $R^6$ is chloro, fluoro, methyl, ethyl, difluoromethyl, hydroxy, methoxy, ethoxy, (methoxy) methyl, (ethoxy) methyl, (methoxy) ethyl, (ethoxy)ethyl, oxetanyl, tetrahydrofuranyl, —C(O)-difluoromethyl, —NH$_2$, or —NH(CO)CH$_3$.

Embodiment 65 provides the method according to any of embodiments 47-57, wherein $R^6$ is halogen, $C_1$-$C_6$ alkyl, or $C_1$-$C_6$ alkoxy; for example, $R^6$ is halogen, $C_1$-$C_3$ alkyl, or $C_1$-$C_3$ alkoxy.

Embodiment 66 provides the method according to any of embodiments 47-57, wherein $R^6$ is chloro, fluoro, methyl, ethyl, methoxy, or ethoxy.

Embodiment 67 provides the method according to any one of embodiments 47-63, wherein $R^7$ is methyl.

Embodiment 68 provides the method according to any one of embodiments 47-63, wherein $R^7$ is ethyl.

Embodiment 69 provides the method according to any one of embodiments 47-63, wherein $R^7$ is propyl (e.g., isopropyl).

Embodiment 70 provides the method according to any one of embodiments 47-63, wherein $R^7$ is difluoromethyl or trifluoromethyl.

Embodiment 71 provides the method according to any of embodiments 47-67, wherein $R^{53}$ is hydrogen or methoxy; or wherein $R^{53}$ is hydrogen.

Embodiment 72 provides the method according to embodiment 47, where the PRMT5 inhibitor is of the formula:

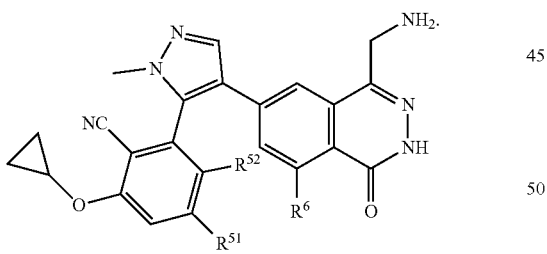

Embodiment 73 provides the method according to any one of embodiments 47-69, wherein $R^{52}$ is fluoro, and $R^{51}$ is hydrogen, fluoro, chloro, or methyl.

Embodiment 74 provides the method according to any one of embodiments 47-69, wherein $R^{52}$ is fluoro, and $R^{51}$ is chloro.

Embodiment 75 provides the method according to any one of embodiments 47-69, wherein $R^{52}$ is fluoro, and $R^{51}$ is methyl or hydrogen (for example, $R^{52}$ is fluoro and $R^{51}$ is methyl; or $R^{52}$ is fluoro and $R^{51}$ is hydrogen).

Embodiment 76 provides the method according to any one of embodiments 47-69, wherein $R^{51}$ and $R^{52}$ together with atoms to which they are attached form a hydrofuranyl (e.g., 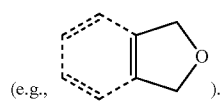).

Embodiment 77 provides the method according to any one of embodiments 47-76, wherein the PRMT5 inhibitor is

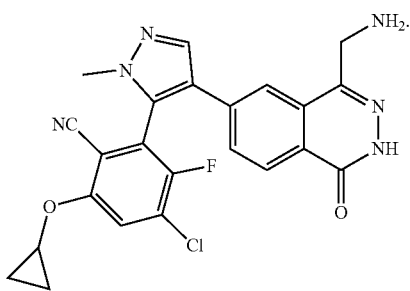 [SMILES: Cn1ncc(-c2ccc3c(=O)[nH]nc(CN)c3c2)c1-c1c(F)c(Cl)cc(OC2CC2)c1C#N]

Embodiment 78 provides the method according to any one of embodiments 47-77, wherein the PRMT5 inhibitor is (MRTX1719)

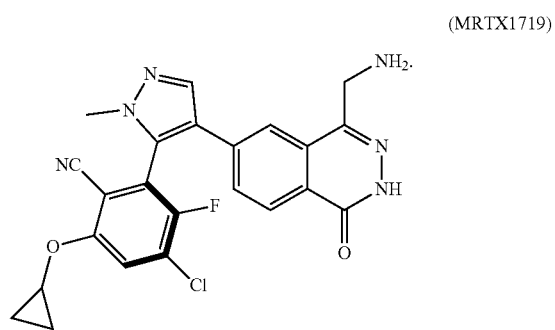

One aspect of the disclosure provides the method wherein the PRMT5 inhibitor is a compound of the formula (IIIA) (Embodiment 79):

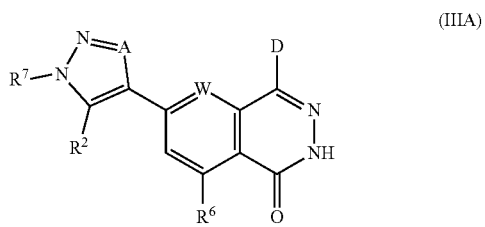

(IIIA)

or a pharmaceutically acceptable salt thereof, wherein

A is CR$^9$ or N;

D is —CH$_2$—NH$_2$,

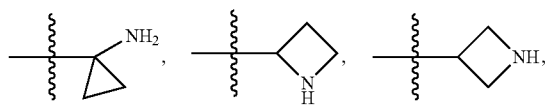

-continued

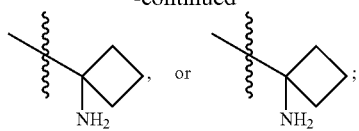

W is CR⁹ or N, where R⁹ is H or $C_1$-$C_3$ alkyl;
R² is

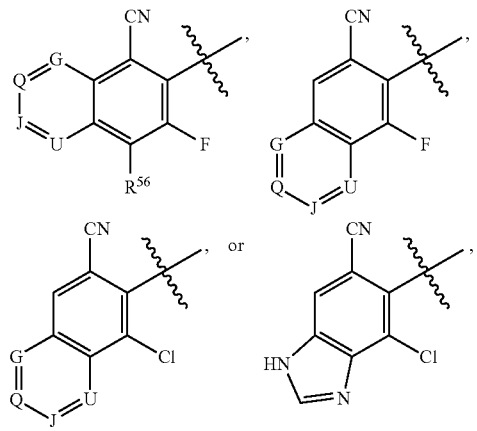

where $R^{56}$ is hydrogen, fluoro, chloro, or methyl,
G, Q, J and U are independently selected from C(H), C($R^5$), and N, provided only one or two of G, Q, J, and U can be N;
each $R^5$ is independently hydroxy, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl;
$R^6$ is hydrogen, halogen, $C_1$-$C_6$ alkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, or —NR¹⁵(CO)R¹⁶, where R¹⁵ is hydrogen or methyl, and R¹⁶ is $C_1$-$C_3$ alkyl; and
$R^7$ is $C_1$-$C_3$ alkyl or $C_1$-$C_3$ haloalkyl.

One aspect of the disclosure provides the method wherein the PRMT5 inhibitor is a compound of the formula (IIIA) (Embodiment 80):

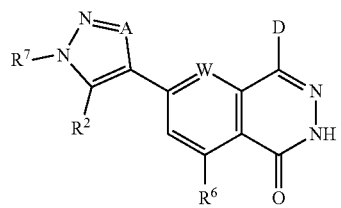
(IIIA)

or a pharmaceutically acceptable salt thereof, wherein
A is CR⁹ or N;
D is —CH₂—NH₂,

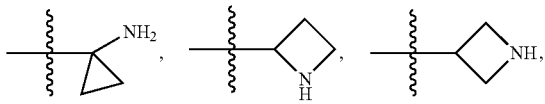

-continued

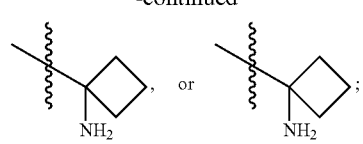

W is CR⁹ or N, where R⁹ is H or $C_1$-$C_3$ alkyl;
R² is

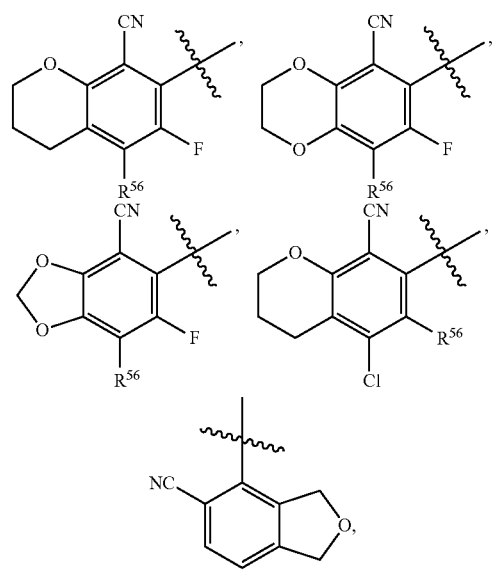

where $R^{56}$ is hydrogen, halogen, $C_1$-$C_6$ alkyl, $C_1$-$C_6$ haloalkyl, $C_1$-$C_6$ alkoxy, or $C_1$-$C_6$ haloalkoxy;
$R^6$ is hydrogen, halogen, $C_1$-$C_6$ alkyl, hydroxy, $C_1$-$C_6$ alkoxy, $C_1$-$C_3$ alkoxy$C_1$-$C_3$ alkyl, $C_3$-$C_6$ heterocycloalkyl, —C(O)—$C_1$-$C_3$ haloalkyl, or —NR¹⁵(CO)R¹⁶, where R¹⁵ is hydrogen or methyl, and R¹⁶ is $C_1$-$C_3$ alkyl; and
$R^7$ is $C_1$-$C_3$ alkyl or $C_1$-$C_3$ haloalkyl.

Embodiment 81 provides the method according to embodiment 79 or 80, wherein A is CH.

Embodiment 82 provides the method according to embodiment 79 or 80, wherein W is N.

Embodiment 83 provides the method according to embodiment 79 or 80, wherein W is CH.

Embodiment 84 provides the method according to any of embodiments 79 or 80, wherein D is —CH₂—NH₂.

Embodiment 85 provides the method according to embodiment 79 or 80, which is of the formula:

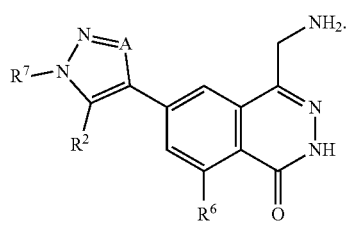

Embodiment 86 provides the method according to embodiment 79 or 81-85, wherein $R^2$ is

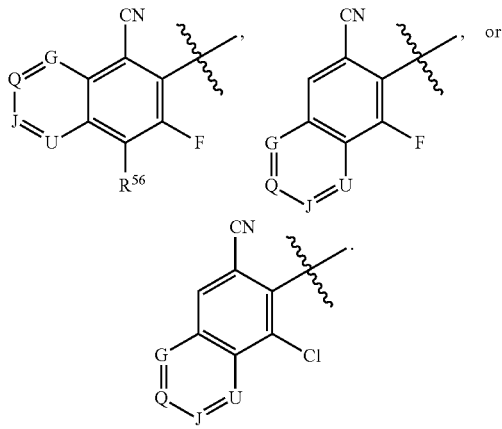

Embodiment 87 provides the method according to embodiment 86, wherein G, Q, J and U are independently selected from C(H) and C($R^5$).

Embodiment 88 provides the method according to embodiment 86, wherein G, Q, J and U are independently C(H).

Embodiment 89 provides the method according to embodiment 86, wherein at least one of G, Q, J, and U is C($R^5$), and the remaining G, Q, J, and U are independently C(H); for example only one of G, Q, J, and U is C($R^5$).

Embodiment 90 provides the method according to embodiment 86, wherein U is N, and G, Q, and J are independently selected from C(H) and C($R^5$).

Embodiment 91 provides the method according to embodiment 86, wherein G is N, and Q, J, and U are independently selected from C(H) and C($R^5$).

Embodiment 92 provides the method according to any one of embodiments 79 or 81-91, wherein $R^5$, if present, is hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ cycloalkoxy, $C_3$-$C_6$ cycloalkyl, $C_3$-$C_6$ heterocycloalkyl, or $C_1$-$C_3$ alkoxy$C_1$-$C_3$ alkyl.

Embodiment 93 provides the method according to any one of embodiments 79 or 81-91, wherein $R^5$, if present, is hydroxy, halogen, $C_1$-$C_3$ alkyl, $C_1$-$C_3$ haloalkyl, $C_1$-$C_3$ alkoxy, $C_1$-$C_3$ haloalkoxy, $C_3$-$C_6$ heterocycloalkyl, or $C_1$-$C_3$ alkoxy$C_1$-$C_3$ alkyl.

Embodiment 94 provides the method according to any one of embodiments 79 or 81-91, wherein $R^5$, if present, is hydroxy, chloro, fluoro, methyl, ethyl, methoxy, ethoxy, 2,2-difluoroethoxy, oxetanyl, tetrahydrofuranyl, (methoxy)methyl, (ethoxy)methyl, (methoxy)ethyl, or (ethoxy)ethyl.

Embodiment 95 provides the method according to any one of embodiments 79 or 81-91, wherein $R^5$, if present, is halogen, $C_1$-$C_6$ alkyl, or $C_1$-$C_6$ alkoxy; for example, $R^6$ is halogen, $C_1$-$C_3$ alkyl, or $C_1$-$C_3$ alkoxy.

Embodiment 96 provides the method according to any one of embodiments 79 or 81-91, wherein $R^5$, if present, is chloro, fluoro, methyl, ethyl, methoxy, or ethoxy.

Embodiment 97 provides the method according to any one of embodiments 79 or 81-91, wherein $R^{56}$ is fluoro, chloro, or methyl.

Embodiment 98 provides the method according to embodiment 80-85, wherein $R^2$ is

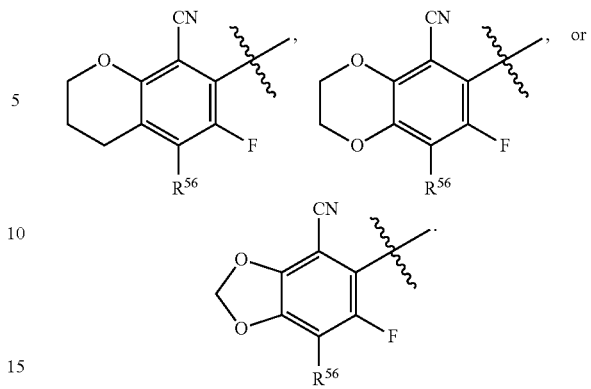

Embodiment 99 provides the method according to any of embodiments 80-85 or 98, wherein $R^{56}$ is hydrogen, fluoro, chloro, or methyl.

Embodiment 100 provides the method according to any of embodiments 79-99, wherein $R^6$ is hydrogen, halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —N$R^{15}$(CO)$R^{16}$; for example, wherein $R^6$ is hydrogen, chloro, fluoro, methyl, ethyl, difluoromethyl, hydroxy, methoxy, ethoxy, (methoxy)methyl, (ethoxy) methyl, (methoxy)ethyl, (ethoxy)ethyl, oxetanyl, tetrahydrofuranyl, —C(O)-difluoromethyl, —NH$_2$, or —NH(CO)CH$_3$.

Embodiment 101 provides the method according to any of embodiments 79-99, wherein $R^6$ is hydrogen, halogen, $C_1$-$C_6$ alkyl, or $C_1$-$C_6$ alkoxy; for example, $R^6$ is hydrogen, halogen, $C_1$-$C_3$ alkyl, or $C_1$-$C_3$ alkoxy.

Embodiment 102 provides the method according to any of embodiments 79-99, wherein $R^6$ is hydrogen, chloro, fluoro, methyl, ethyl, methoxy, or ethoxy.

Embodiment 103 provides the method according to any of embodiments 79-99, wherein $R^6$ is halogen, $C_1$-$C_3$ alkyl, $C_1$-$C_3$ haloalkyl, hydroxy, $C_1$-$C_3$ alkoxy, $C_1$-$C_3$ alkoxy$C_1$-$C_3$ alkyl, $C_3$-$C_6$ heterocycloalkyl, —C(O)—$C_1$-$C_3$ haloalkyl, —N($R^9$)$_2$, or —N$R^{15}$(CO)$R^{16}$; for example, wherein $R^6$ is chloro, fluoro, methyl, ethyl, difluoromethyl, hydroxy, methoxy, ethoxy, (methoxy) methyl, (ethoxy) methyl, (methoxy) ethyl, (ethoxy)ethyl, oxetanyl, tetrahydrofuranyl, —C(O)-difluoromethyl, —NH$_2$, or —NH(CO)CH$_3$.

Embodiment 104 provides the method according to any of embodiments 79-99, wherein $R^6$ is halogen, $C_1$-$C_6$ alkyl, or $C_1$-$C_6$ alkoxy; for example, $R^6$ is halogen, $C_1$-$C_3$ alkyl, or $C_1$-$C_3$ alkoxy.

Embodiment 105 provides the method according to any of embodiments 79-99, wherein $R^6$ is chloro, fluoro, methyl, ethyl, methoxy, or ethoxy.

Embodiment 106 provides the method according to any one of embodiments 79-105, wherein $R^7$ is methyl.

Embodiment 107 provides the method according to any one of embodiments 79-105, wherein $R^7$ is ethyl.

Embodiment 108 provides the method according to any one of embodiments 79-105, wherein $R^7$ is propyl (e.g., isopropyl).

Embodiment 109 provides the method according to any one of embodiments 79-105, wherein $R^7$ is difluoromethyl or trifluoromethyl.

In certain embodiments of the methods of the disclosure as described herein, the PRMT5 inhibitor is:

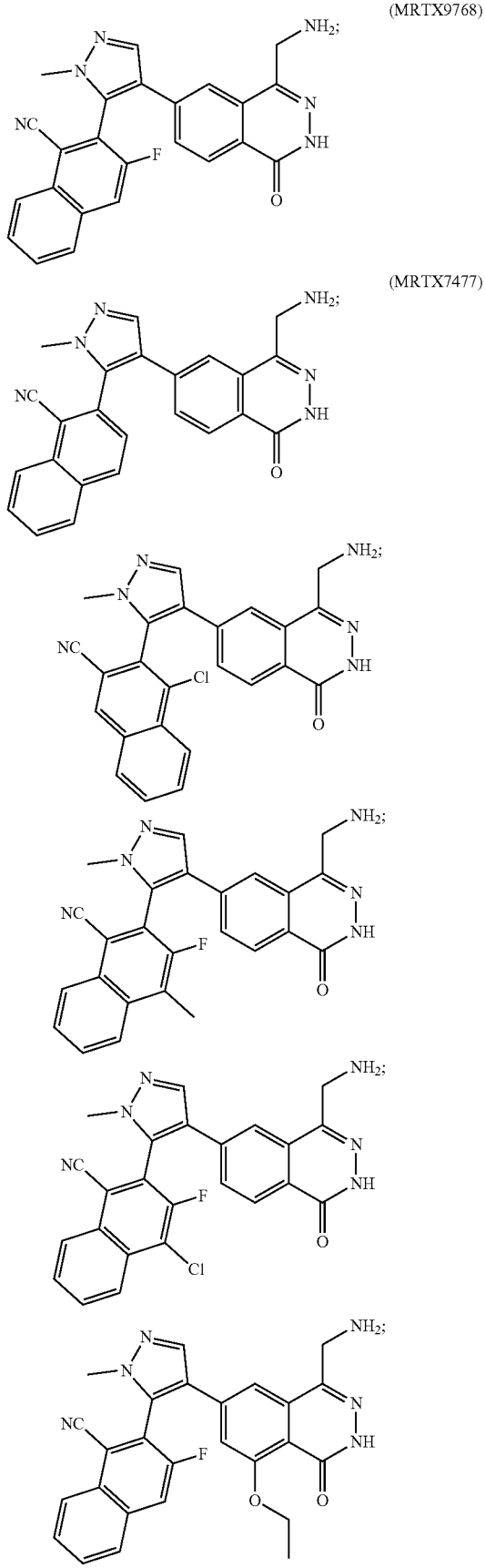
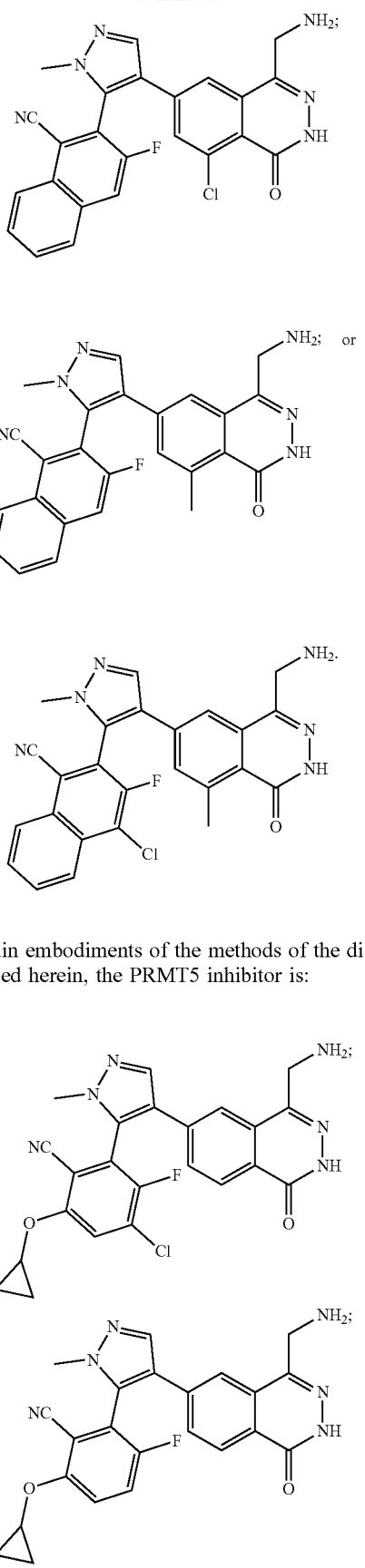
In certain embodiments of the methods of the disclosure as described herein, the PRMT5 inhibitor is:

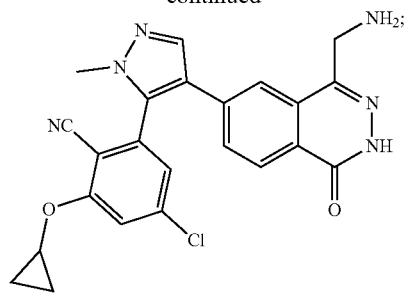
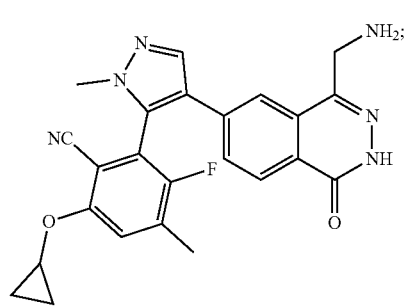
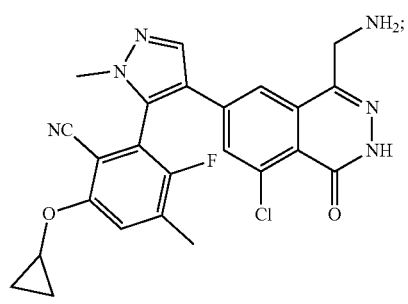
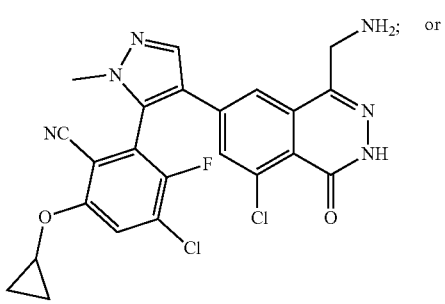
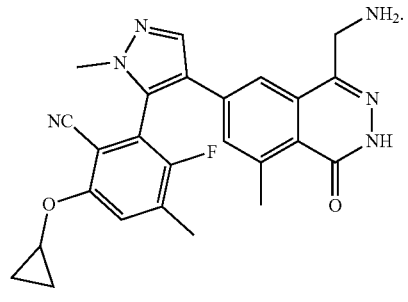
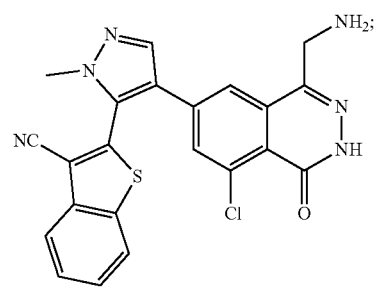
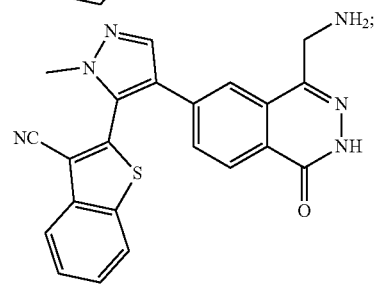
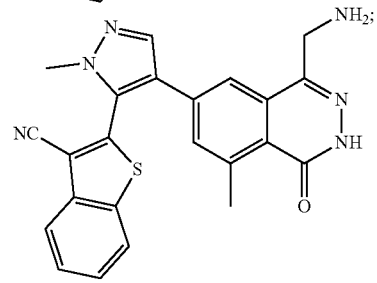
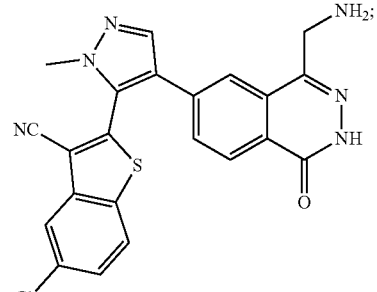
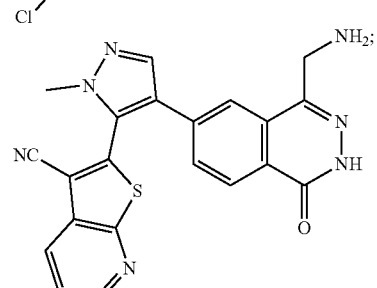
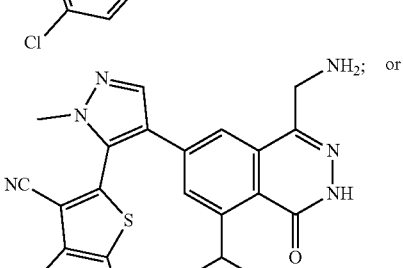
In certain embodiments of the methods of the disclosure as described herein, the PRMT5 inhibitor is:

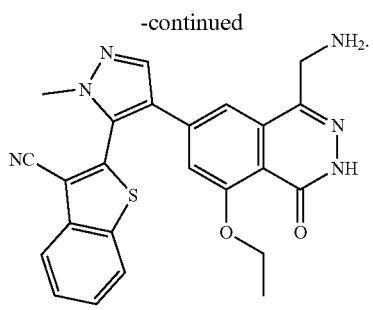

In certain embodiments of the methods of the disclosure as described herein, the PRMT5 inhibitor is:

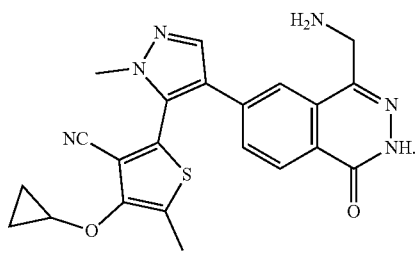 [SMILES: Cc1sc(-c2c(-c3ccc4c(=O)[nH]nc(CN)c4c3)cnn2C)c(C#N)c1OC1CC1]

The PRMT5 inhibitor of the disclosure and/or the CDK4/6 inhibitor of the disclosure may be provided as a pharmaceutical composition comprising a therapeutically effective amount of such inhibitor and a pharmaceutically acceptable carrier, excipient, and/or diluents. The PRMT5 inhibitor of the disclosure and/or the CDK4/6 inhibitor of the disclosure may be formulated by any method well known in the art and may be prepared for administration by any route, including, without limitation, parenteral, oral, sublingual, transdermal, topical, intranasal, intratracheal, or intrarectal. In certain embodiments, The PRMT5 inhibitor of the disclosure and/or the CDK4/6 inhibitor of the disclosure are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, pharmaceutical compositions of the disclosure may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The PRMT5 inhibitor and the CDK4/6 inhibitor of the disclosure are administered in a therapeutically effective amount. As used herein, the phrase "therapeutically effective amount" or "effective amount" refers to the amount of active agent that elicits the biological or medicinal response that is being sought in a tissue, system, subject or human by a researcher, medical doctor or other clinician. In general, the therapeutically effective amount is sufficient to deliver the biological or medicinal response to the subject without causing serious toxic effects. A dose of the active agent may be in the range from about 0.01 to 300 mg/kg per day, such as 0.1 to 100 mg/kg per day, more generally 0.5 to about 25 mg/kg body weight of the recipient per day. A typical topical dosage will range from 0.01 to 3% wt/wt in a suitable carrier.

In certain embodiments of the methods of the disclosure, the therapeutically effective amount of the PRMT5 inhibitor is in the range of about 0.01 to 300 mg/kg per day. For example, in certain embodiments, the therapeutically effective amount of the PRMT5 inhibitor is in the range of about 0.1 to 100 mg/kg per day, or 25 to 100 mg/kg per day, or 50 to 100 mg/kg per day.

In certain embodiments, the therapeutically effective amount of the PRMT5 inhibitor is less than 1% of, e.g., less than 10%, or less than 25%, or less than 50% of the clinically-established therapeutic amount (e.g., such as the amount required when the PRMT5 inhibitor is administered by itself).

In certain embodiments of the methods of the disclosure, the therapeutically effective amount of the CDK4/6 inhibitor is in the range of about 0.01 to 300 mg/kg per day. For example, in certain embodiments, the therapeutically effective amount of the CDK4/6 inhibitor is in the range of about 0.1 to 100 mg/kg per day, or 0.1 to 50 mg/kg per day, or 10 to 100 mg/kg per day, or 10 to 50 mg/kg per day.

In certain embodiments, the therapeutically effective amount of the CDK4/6 inhibitor is less than 1% of, e.g., less than 10%, or less than 25%, or less than 50% of the clinically-established therapeutic amount (e.g., such as the amount required when the CDK4/6 inhibitor is administered by itself).

Combination therapy, in defining use of PRMT5 inhibitor and the CDK4/6 inhibitor of the present disclosure, is intended to embrace administration of each agent in a sequential manner in a regimen that will provide beneficial effects of the drug combination (e.g., the PRMT5 inhibitor and the CDK4/6 inhibitor of the disclosure can be formulated as separate compositions that are given sequentially), and is intended as well to embrace co-administration of these agents in a substantially simultaneous manner, such as in a single dosage form having a fixed ratio of these active agents or in multiple or a separate dosage forms for each agent. The disclosure is not limited in the sequence of administration: the PRMT5 inhibitor of the disclosure may be administered either prior to or after (i.e., sequentially), or at the same time (i.e., simultaneously) as administration of the CDK4/6 inhibitor of the disclosure.

The methods of disclosure are useful as a first-line treatment. Thus, in certain embodiments of the methods of the disclosure, the subject has not previously received another first-line of therapy.

The methods of disclosure are also useful as a first-line maintenance or a second-line treatment. Thus, in certain embodiments of the methods of the disclosure, the subject has previously completed another first-line of therapy. For example, the methods of the disclosure, in certain embodiments, may provide a delay in progression and relapse of cancer in subjects that have previously completed another first-line chemotherapy. For example, in certain embodiments, the subject has previously completed a platinum- and/or taxane-based chemotherapy (e.g., carboplatin, cisplatin, oxaliplatin, paclitaxel, docetaxel, and the like). In certain embodiments of the methods of the disclosure, the subject has previously completed another first-line chemotherapy and is in partial response to such chemotherapy.

Definitions

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

The term "amino" refers to —$NH_2$.

The term "acetyl" refers to "—$C(O)CH_3$.

As herein employed, the term "acyl" refers to an alkylcarbonyl or arylcarbonyl substituent wherein the alkyl and aryl portions are as defined herein.

The term "alkyl" as employed herein refers to saturated straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —$OC_1$-$C_6$ alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or $NR^x$, wherein $R^x$ is hydrogen or $C_1$-$C_3$ alkyl. Examples of heteroalkyl groups include methoxymethyl, methoxyethyl and methoxypropyl.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl. An "aryl" group also includes fused multicyclic (e.g., bicyclic) ring systems in which one or more of the fused rings is non-aromatic, provided that at least one ring is aromatic, such as indenyl.

An "aralkyl" or "arylalkyl" group comprises an aryl group covalently linked to an alkyl group wherein the moiety is linked to another group via the alkyl moiety. An exemplary aralkyl group is —$(C_1$-$C_6)$alkyl$(C_6$-$C_{10})$aryl, including, without limitation, benzyl, phenethyl, and naphthylmethyl. For example, an ar$C_1$-$C_3$alkyl is an aryl group covalently linked to a $C_1$-$C_3$ alkyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, N, $NR^4$, O, or S, and the remainder of the ring atoms are quaternary or carbonyl carbons. Examples of heterocyclic groups include, without limitation, epoxy, oxiranyl, oxetanyl, azetidinyl, aziridinyl, tetrahydrofuranyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

As used herein, "L-heterocyclyl" refers to a heterocyclyl group covalently linked to another group via an alkylene linker.

As used herein, the term "heteroaryl" refers to a group having 5 to 14 ring atoms, preferably 5, 6, 10, 13 or 14 ring atoms; having 6, 10, or 14π electrons shared in a cyclic array; and having, in addition to carbon atoms, from one to three heteroatoms that are each independently N, O, or S. Heteroaryl also includes fused multicyclic (e.g., bicyclic) ring systems in which one or more of the fused rings is non-aromatic, provided that at least one ring is aromatic and at least one ring contains an N, O, or S ring atom. Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "L-heteroaralkyl" or "L-heteroarylalkyl" group comprises a heteroaryl group covalently linked to another group via an alkylene linker. Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is a bivalent aryl, heteroaryl, or heterocyclyl group, respectively, as defined hereinabove, that is positioned between and serves to connect two other chemical groups.

As employed herein, when a moiety (e.g., cycloalkyl, aryl, heteroaryl, heterocyclyl, urea, etc.) is described as "optionally substituted" without expressly stating the substituents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, chloromethyl, and fluoromethyl.

The term "hydroxyalkyl" refers to -alkylene-OH.

EXAMPLE

The methods of the disclosure are illustrated further by the following examples, which is not to be construed as limiting the disclosure in scope or spirit to the specific procedures and compounds described in them.

Study Design

The PRMT5 inhibitors of the disclosure demonstrate selective activity in MTAP-deleted cancers by binding to and further inhibiting PRMT5 when bound to the intracellular metabolite MTA. As noted above, MTAP is an enzyme in the methionine salvage pathway and its deletion in cancer cells leads to the accumulation of MTA in these cells. PRMT5 is an essential enzyme required for cell viability and, as such, the PRMT5 inhibitors of the disclosure represent a novel approach to selectively treat MTAP-deleted cancers.

A single mutation will likely not cause cancer—most often, it is multiple mutations that are responsible for developing cancer. The inventors found the treatment of certain cancers with PRMT5 inhibitors improved with the use of combination therapies. Particularly, the inventors surprisingly found that a combination therapy of PRMT5 inhibitor and CDK4/6 inhibitor provides greater antitumor activity compared to either inhibitor alone.

Study Procedure

Immunodeficient female nu/nu mice were implanted with $5 \times 10^6$ LU99 lung cancer cells in 50% Matrigel. Tumors were measured using calipers until they reached approximately 150-200 $mm^3$. Animals were randomized to receive A) vehicle (0.5% methylcellulose (4000 cps)/0.2% Tween80 in water), B) a PRMT5 inhibitor, C) CDK4/6 inhibitor, or D) the PRMT5 inhibitor and CDK4/6 inhibitor, all administered orally (PO) for 21 days. Tumor volume was measured twice a week (n=5/treatment group). Average tumor volume and standard error of the mean was calculated and plotted at each study day in GraphPad.

Example 1

This example was carried out according to the study procedure described above. The PRMT5 inhibitor was MRTX9768 administered at 100 mg/kg twice a day (BID). MRTX9768 is 2-(4-(4-(aminomethyl)-1-oxo-1,2-dihydrophthalazin-6-yl)-1-methyl-1H-pyrazol-5-yl)-3-fluoro-1-naphthonitrile, disclosed as Example 16-1 at p. 304 of the International patent publication No. WO 2021/050915 A1, published 18 Mar. 2021, incorporated by reference in its entirety.

The CDK4/6 inhibitor used in this example was palbociclib administered at 130 mg/kg once a day (QD). Palbociclib is 6-acetyl-8-cyclopentyl-5-methyl-2-[(5-piperazin-1-ylpyridin-2-yl)amino]pyrido[2,3-d]pyrimidin-7-one, and is sold as Ibrance® available from Pfizer Inc., New York, New York.

Results are provided in FIG. 1 and Table 1. The combination of MRTX9768 and MRTX849 led to greater antitumor activity compared to either inhibitor alone in this $KRAS^{G12C}$ and $CDKN2A/MTAP^{DEL}$ lung tumor xenograft LU99 model.

TABLE 1

| | | Tumor Volume ($mm^3$) | | | | | | |
|---|---|---|---|---|---|---|---|---|
| Group | Day | 0 | 3 | 7 | 10 | 14 | 17 | 21 |
| Vehicle | Mean | 181.04 | 276.67 | 467.48 | 718.83 | 1040.93 | 1358.61 | 1951.06 |
| (PO QD) | SEM | 18.84 | 29.58 | 61.05 | 103.76 | 215.23 | 266.16 | 306.05 |
| MRTX9768 | Mean | 183.59 | 265.26 | 331.80 | 349.53 | 406.58 | 431.91 | 458.95 |
| (100 mg/kg PO BID) | SEM | 15.07 | 16.07 | 24.14 | 25.13 | 43.52 | 51.50 | 60.11 |
| palbociclib | Mean | 184.39 | 247.02 | 355.77 | 482.60 | 731.56 | 914.41 | 1148.44 |
| (130 mg/kg PO QD) | SEM | 15.37 | 29.94 | 47.97 | 58.36 | 93.09 | 114.17 | 133.46 |
| MRTX9768 | Mean | 184.20 | 262.26 | 287.14 | 309.96 | 335.73 | 335.87 | 298.87 |
| (100 mg/kg PO BID) + palbociclib (130 mg/kg PO QD) | SEM | 15.75 | 20.21 | 24.40 | 27.65 | 24.97 | 27.15 | 39.04 |

Example 2

This example was carried out according to the study procedure described above. The PRMT5 inhibitor was MRTX7477, administered at 200 mg/kg BID. MRTX7477 is 24444-(aminomethyl)-1-oxo-1,2-dihydrophthalazin-6-yl)-

1-methyl-1H-pyrazol-5-yl)-1-naphthonitrile, disclosed as Example 4-147 at p. 226 of the International patent publication No. WO 2021/050915 A1, published 18 Mar. 2021, incorporated by reference in its entirety. The CDK4/6 inhibitor used in this example was the same as in Example 1, palbociclib, administered at 130 mg/kg QD.

Figure 2:
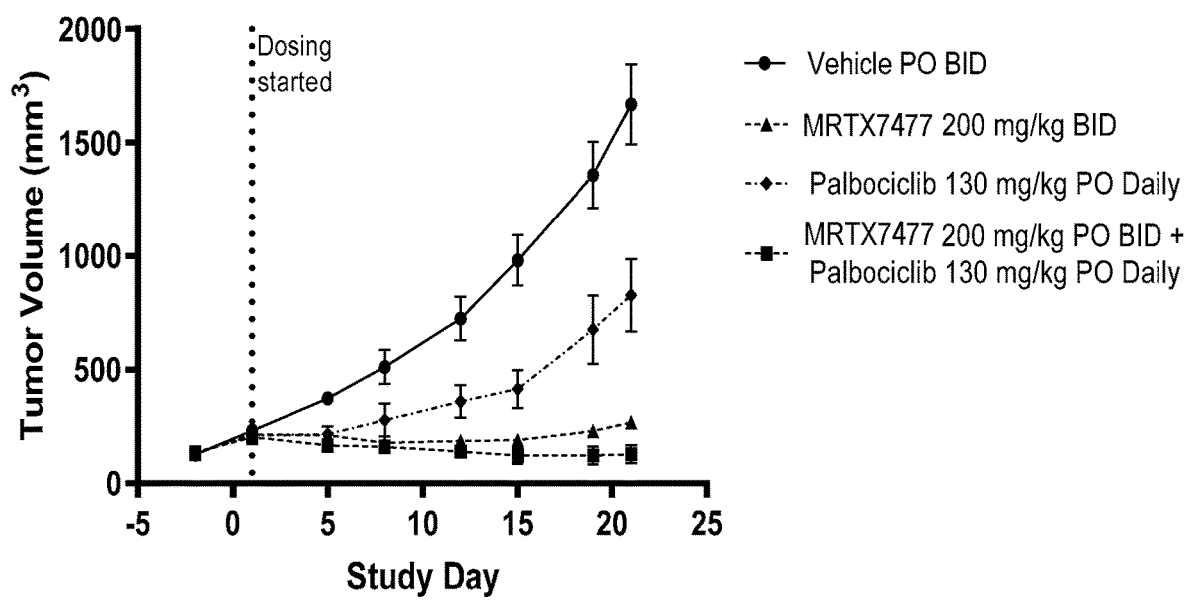
FIG. 2 illustrates the results of the methods of Example 2 in the $KRAS^{G12C}$ and $CDKN2A/MTAP^{DEL}$ lung tumor xenograft LU99 model grown in immunodeficient mice. The PRMT5 inhibitor used in this method was MRTX7477 administered at 200 mg/kg BID, and the CDK4/6 inhibitor was palbociclib administered at 130 mg/kg QD. Average tumor volume±standard error is plotted of the mean at study day as indicated.

Results are provided in FIG. 2 and Table 2. The combination of MRTX7477 and MRTX849 led to greater antitumor activity compared to either inhibitor alone in this KRAS$^{G12C}$ and CDKN2A/MTAP$^{DEL}$ lung tumor xenograft LU99 model.

TABLE 2

| Group | Tumor Volume (mm³) | | | | | | | |
|---|---|---|---|---|---|---|---|---|
| | −2 | 1 | 5 | 8 | 12 | 15 | 19 | 21 |
| Vehicle (PO QD) | 126.3 | 230.8 | 372.8 | 511.0 | 724.4 | 981.3 | 1357.6 | 1669.9 |
| MRTX7477 (200 mg/kg PO BID) | 129.4 | 214.5 | 210.7 | 177.1 | 185.3 | 189.1 | 229.5 | 267.5 |
| Palbociclib (130 mg/kg PO QD) | 133.4 | 209.8 | 215.9 | 277.3 | 359.4 | 413.5 | 675.9 | 827.0 |
| MRTX7477 (200 mg/kg PO BID) + palbociclib (130 mg/kg PO QD) | 135.3 | 203.1 | 165.8 | 159.4 | 138.5 | 122.8 | 123.2 | 127.7 |

Examples 3 to 6

The compound of the disclosure was evaluated in several different lung tumor xenograft models: HCC4006, SW1573 PRMT5-044, H1650, and A549 PRMT-034. This example was carried out substantially according to the study procedure described above, except with mice bearing HCC4006 xenograft tumors, SW1573 PRMT5-044 xenograft tumors, H1650 xenograft tumors, or A549 PRMT-034 xenograft tumors. The PRMT5 inhibitor was MRTX1719, administered at 50 mg/kg QD or at 100 mg/kg QD. MRTX1719 is (2M)-2-(4-(4-(aminomethyl)-1-oxo-1,2-dihydrophthalazin-6-yl)-1-methyl-1H-pyrazol-5-yl)-4-chloro-6-cyclopropoxy-3-fluorobenzonitrile, disclosed as Example 16-8 at p. 307 of the International patent publication No. WO 2021/050915 A1, published 18 Mar. 2021, incorporated by reference in its entirety. The CDK4/6 inhibitor used in this example was the same as in Example 1, palbociclib, administered at 130 mg/kg QD.

Figure 3:
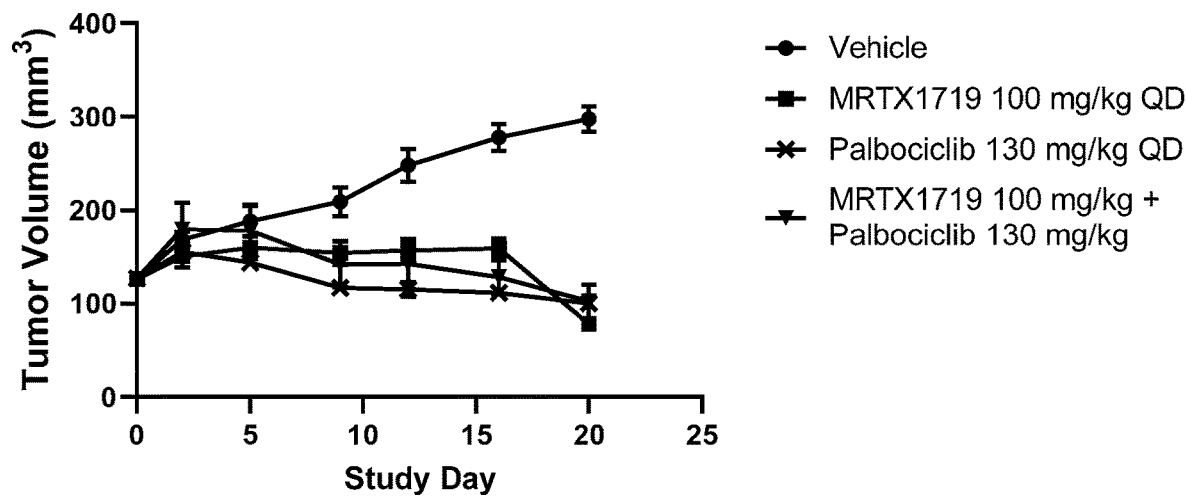
FIG. 3 illustrates the results of the methods of Example 3 in HCC4006 lung tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The results for HCC4006 are provided in FIG. 3 and Table 3.

TABLE 3

| Group | | Tumor Volume (mm³) | | | | | | |
|---|---|---|---|---|---|---|---|---|
| | Day | 0 | 2 | 5 | 9 | 12 | 16 | 20 |
| Vehicle (PO QD) | Mean | 126 | 168 | 188 | 209 | 248 | 278 | 297 |
| | SEM | 6 | 9 | 16 | 15 | 18 | 15 | 14 |
| MRTX1719 (100 mg/kg PO QD) | Mean | 126 | 150 | 159 | 154 | 156 | 159 | 78 |
| | SEM | 7 | 12 | 12 | 13 | 10 | 11 | 7 |
| Palbociclib (130 mg/kg PO QD) | Mean | 127 | 155 | 143 | 117 | 115 | 111 | 100 |
| | SEM | 7 | 10 | 7 | 7 | 8 | 5 | 6 |
| MRTX1719 (100 mg/kg PO QD) + Palbociclib (130 mg/kg PO QD) | Mean | 127 | 180 | 178 | 141 | 142 | 128 | 102 |
| | SEM | 8 | 28 | 29 | 25 | 27 | 18 | 18 |

Figure 4:
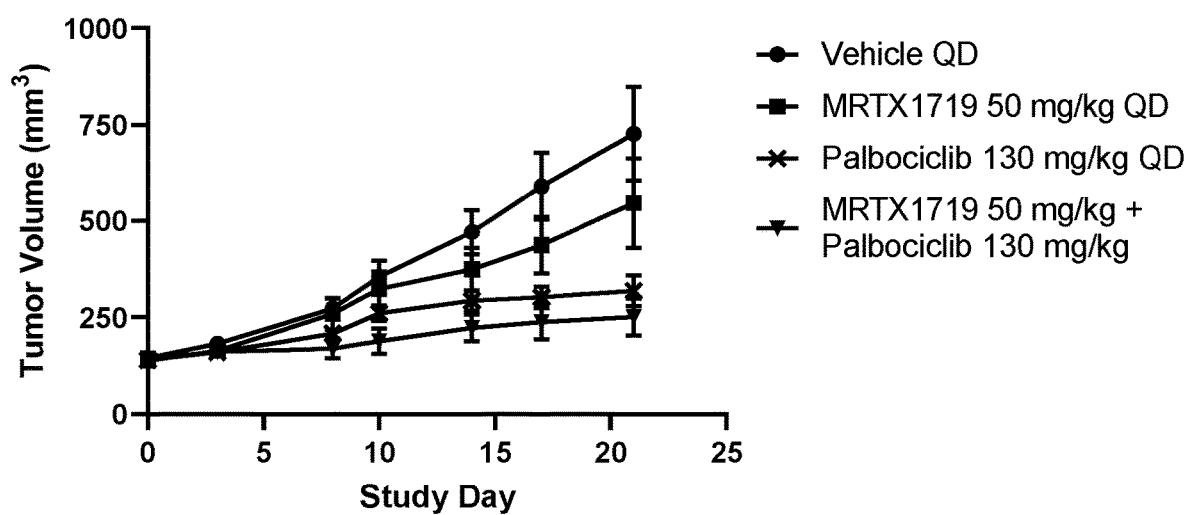
FIG. 4 illustrates the results of the methods of Example 4 in SW1573 PRMT5-044 lung tumor xenograft model. The PRMT5 inhibitor used in this method was MRTX1719 administered at 50 mg/kg QD, and the CDK4/6 inhibitor was palbociclib administered at 130 mg/kg QD. Average tumor volume±standard error is plotted of the mean at study day as indicated.

The results for SW1573 PRMT5-044 are provided in FIG. 4 and Table 4.

TABLE 4

| Grroup | | Tumor Volume (mm³) | | | | | | |
|---|---|---|---|---|---|---|---|---|
| | Day | 0 | 3 | 8 | 10 | 14 | 17 | 21 |
| Vehicle (PO QD) | Mean | 145 | 182 | 273 | 355 | 471 | 590 | 727 |
| | SEM | 12 | 9 | 27 | 42 | 57 | 87 | 121 |
| MRTX1719 (50 mg/kg PO QD) | Mean | 138 | 163 | 259 | 324 | 375 | 437 | 547 |
| | SEM | 9 | 19 | 40 | 46 | 55 | 72 | 117 |
| Palbociclib (130 mg/kg PO QD) | Mean | 140 | 160 | 208 | 260 | 293 | 302 | 319 |
| | SEM | 9 | 10 | 17 | 20 | 25 | 28 | 40 |

TABLE 4-continued

| Grroup | | Tumor Volume (mm³) | | | | | | |
|---|---|---|---|---|---|---|---|---|
| | Day | 0 | 3 | 8 | 10 | 14 | 17 | 21 |
| MRTX1719 (50 mg/kg PO QD) + Palbociclib (130 mg/kg PO QD) | Mean | 143 | 162 | 170 | 189 | 223 | 238 | 251 |
| | SEM | 10 | 18 | 25 | 33 | 34 | 44 | 48 |

Figure 5:
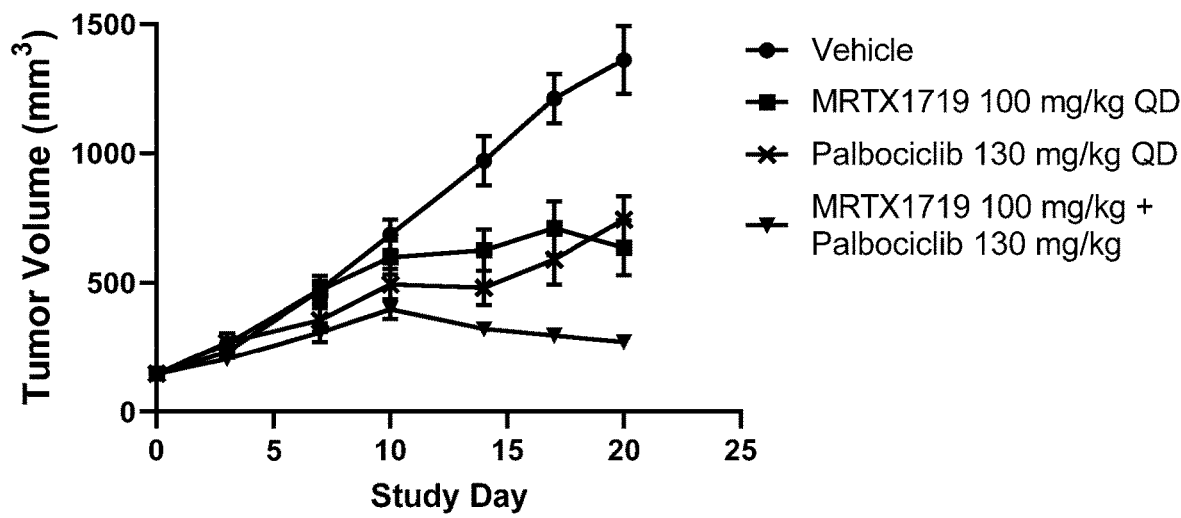
FIG. 5 illustrates the results of the methods of Example 5 in H1650 lung tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The results for H1650 are provided in FIG. 5 and Table 5.

TABLE 5

| Grroup | | Tumor Volume (mm³) | | | | | | |
|---|---|---|---|---|---|---|---|---|
| | Day | 0 | 3 | 7 | 10 | 14 | 17 | 20 |
| Vehicle (PO QD) | Mean | 147 | 264 | 473 | 685 | 971 | 1210 | 1361 |
| | SEM | 12 | 19 | 54 | 58 | 97 | 96 | 131 |
| MRTX1719 (100 mg/kg PO QD) | Mean | 146 | 231 | 471 | 599 | 625 | 711 | 635 |
| | SEM | 11 | 15 | 38 | 66 | 80 | 104 | 107 |
| Palbociclib (130 mg/kg PO QD) | Mean | 147 | 268 | 356 | 493 | 480 | 589 | 743 |
| | SEM | 11 | 37 | 48 | 61 | 67 | 97 | 90 |
| MRTX1719 (100 mg/kg PO QD) + Palbociclib (130 mg/kg PO QD) | Mean | 147 | 204 | 307 | 398 | 322 | 296 | 271 |
| | SEM | 8 | 22 | 37 | 38 | 26 | 24 | 21 |

Figure 6:
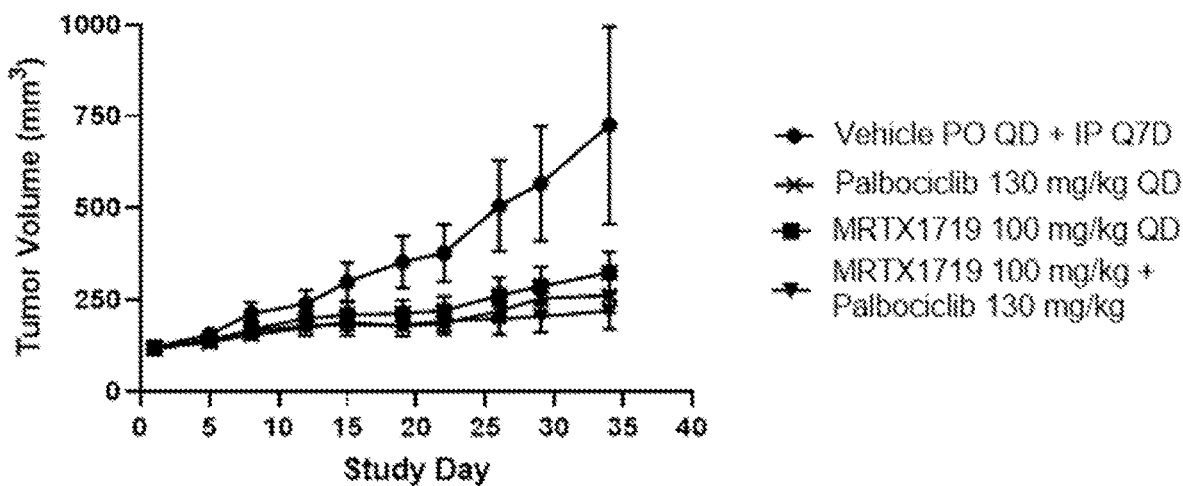
FIG. 6 illustrates the results of the methods of Example 6 in A549 PRMT-034 lung tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The results for A549 PRMT-034 are provided in FIG. 6 and Table 6.

TABLE 6

| Group | | Tumor Volume (mm³) | | | | | | | | |
|---|---|---|---|---|---|---|---|---|---|---|
| | Day | 1 | 5 | 8 | 12 | 15 | 19 | 22 | 26 | 29 | 34 |
| Vehicle (PO QD) | Mean | 119 | 157 | 214 | 240 | 300 | 354 | 378 | 506 | 567 | 726 |
| | SEM | 9 | 18 | 31 | 37 | 52 | 71 | 78 | 124 | 156 | 271 |
| MRTX1719 (100 mg/kg PO QD) | Mean | 118 | | 169 | 200 | 210 | 214 | 221 | 263 | 288 | 325 |
| | SEM | 9 | 15 | 24 | 29 | 34 | 36 | 38 | 49 | 52 | 57 |

TABLE 6-continued

| Group | | Day 1 | 5 | 8 | 12 | 15 | 19 | 22 | 26 | 29 | 34 |
|---|---|---|---|---|---|---|---|---|---|---|---|
| Palbociclib (130 mg/kg PO QD) | Mean | 118 | 134 | 155 | 177 | 189 | 179 | 186 | 220 | 255 | 263 |
| | SEM | 8 | 10 | 10 | 17 | 22 | 19 | 21 | 32 | 47 | 48 |
| MRTX1719 (100 mg/kg PO QD) + Palbociclib (130 mg/kg PO QD) | Mean | 119 | 144 | 166 | 180 | 183 | 182 | 194 | 199 | 206 | 220 |
| | SEM | 9 | 11 | 24 | 28 | 29 | 30 | 38 | 42 | 43 | 49 |

Examples 7 and 8

The compound of the disclosure was evaluated in a couple of different pancreatic tumor xenograft models: PANC-05-04 and BXPC-3. This example was carried out substantially according to the study procedure described above, except with mice bearing PANC-05-04 xenograft tumors or BXPC-3 xenograft tumors. The PRMT5 inhibitor and the CDK4/6 inhibitor used in this example were the same as in Example 3: MRTX1719 was administered at 100 mg/kg QD, and palbociclib was administered at 130 mg/kg QD.

Figure 7:
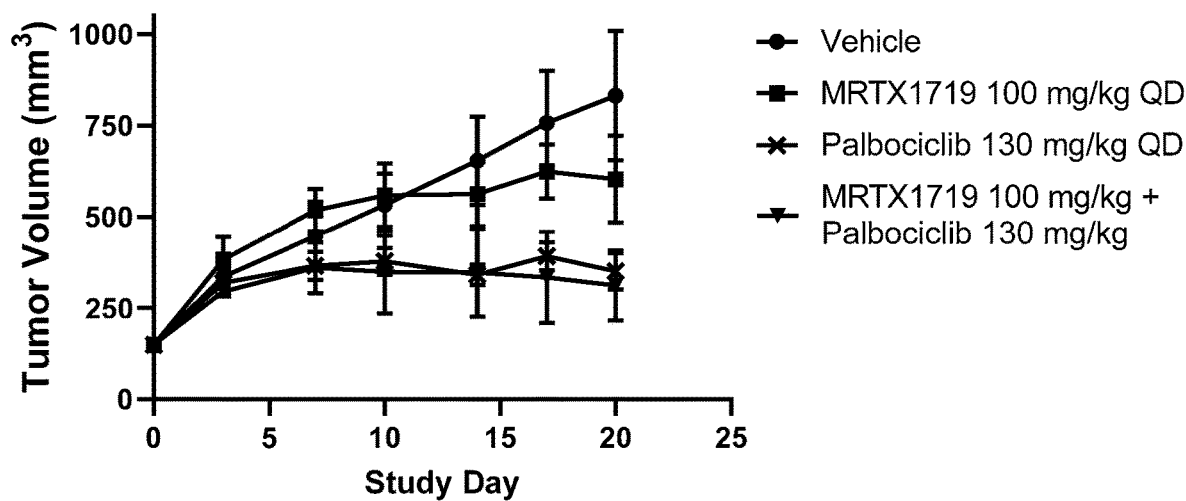
FIG. 7 illustrates the results of the methods of Example 7 in PANC-05-04 pancreatic tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The results for PANC-05-04 are provided in FIG. 7 and Table 7.

TABLE 7

| Group | | Day 0 | 3 | 7 | 10 | 14 | 17 | 20 |
|---|---|---|---|---|---|---|---|---|
| Vehicle (PO QD) | Mean | 150 | 335 | 447 | 534 | 654 | 757 | 832 |
| | SEM | 10 | 50 | 95 | 86 | 121 | 141 | 176 |
| MRTX1719 (100 mg/kg PO QD) | Mean | 149 | 382 | 519 | 559 | 563 | 624 | 603 |
| | SEM | 9 | 63 | 58 | 87 | 88 | 73 | 119 |
| Palbociclib (130 mg/kg PO QD) | Mean | 149 | 319 | 365 | 378 | 341 | 391 | 350 |
| | SEM | 7 | 38 | 39 | 37 | 28 | 39 | 49 |
| MRTX1719 (100 mg/kg PO QD) + Palbociclib (130 mg/kg PO QD) | Mean | 150 | 296 | 360 | 348 | 347 | 334 | 312 |
| | SEM | 7 | 19 | 70 | 114 | 120 | 124 | 96 |

Figure 8:
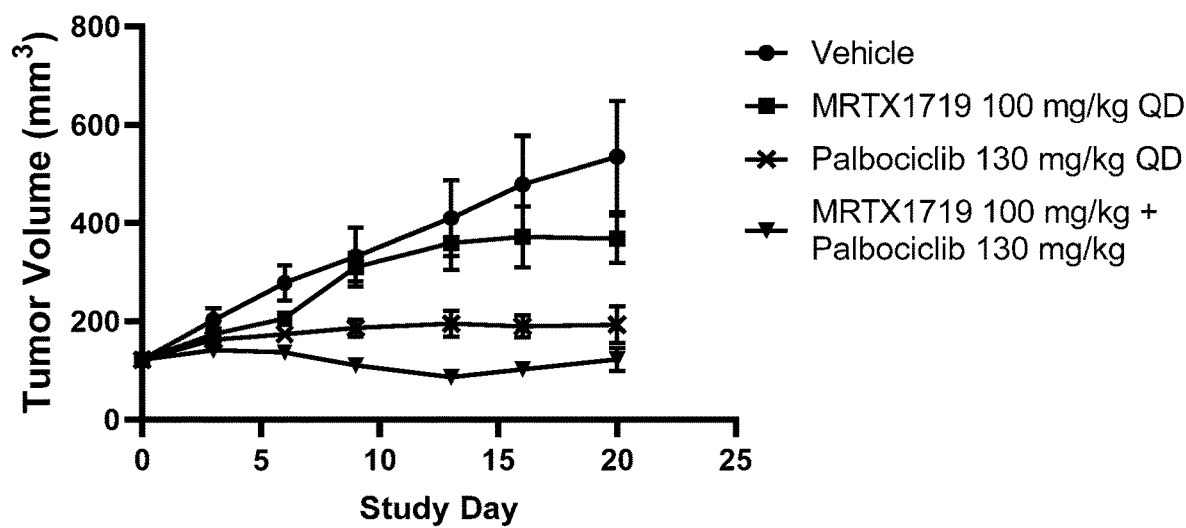
FIG. 8 illustrates the results of the methods of Example 8 in BXPC-3 pancreatic tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The results for BXPC-3 are provided in FIG. 8 and Table 8.

TABLE 8

| Group | | Day 0 | 3 | 6 | 9 | 13 | 16 | 20 |
|---|---|---|---|---|---|---|---|---|
| Vehicle (PO QD) | Mean | 122 | 202 | 277 | 331 | 410 | 479 | 536 |
| | SEM | 9 | 25 | 36 | 60 | 77 | 99 | 112 |
| MRTX1719 (50 mg/kg PO QD) | Mean | 122 | 174 | 206 | 310 | 359 | 372 | 368 |
| | SEM | 10 | 9 | 8 | 29 | 55 | 63 | 49 |
| Palbociclib (130 mg/kg PO QD) | Mean | 122 | 162 | 174 | 187 | 195 | 190 | 193 |
| | SEM | 11 | 10 | 15 | 17 | 27 | 23 | 38 |
| MRTX1719 (50 mg/kg PO QD) + Palbociclib (130 mg/kg PO QD) | Mean | 121 | 141 | 137 | 111 | 86 | 102 | 122 |
| | SEM | 8 | 13 | 13 | 15 | 9 | 4 | 23 |

Example 9

Figure 9:
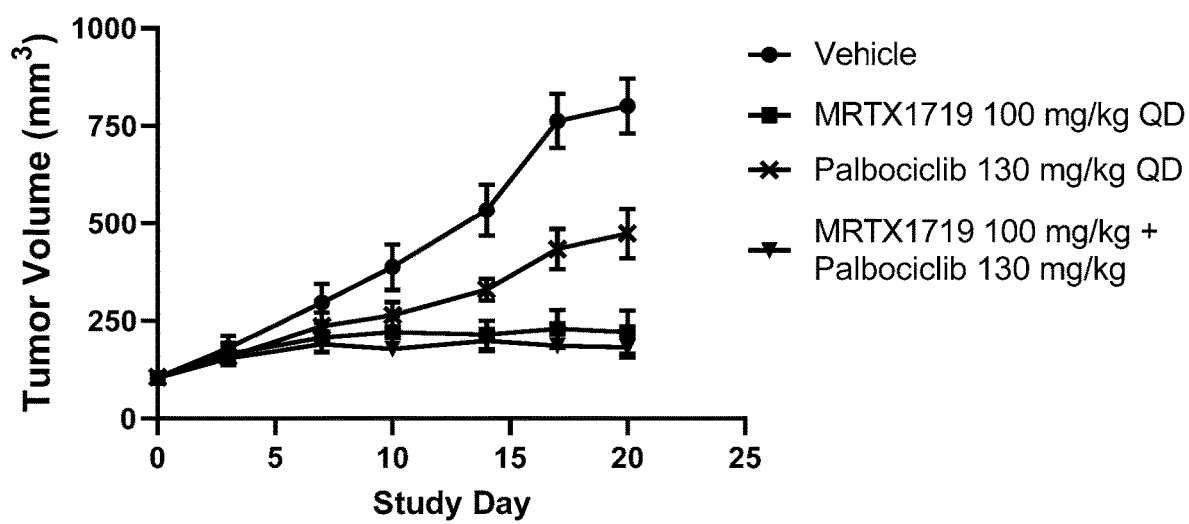
FIG. 9 illustrates the results of the methods of Example 9 in MKN45 gastric tumor xenograft model. The PRMT5 inhibitor used in this method was MRTX1719 administered at 100 mg/kg QD, and the CDK4/6 inhibitor was palbociclib administered at 130 mg/kg QD. Average tumor volume±standard error is plotted of the mean at study day as indicated.

The compound of the disclosure was evaluated in a gastric tumor xenograft model MKN45, and the results are provided in FIG. 9 and Table 9. This example was carried out substantially according to the study procedure described above, except with mice bearing MKN45 xenograft tumors. The PRMT5 inhibitor and the CDK4/6 inhibitor used in this example were the same as in Example 3: MRTX1719 was administered at 100 mg/kg QD, and palbociclib was administered at 130 mg/kg QD.

TABLE 9

| Grroup | | Day 0 | 3 | 7 | 10 | 14 | 17 | 20 |
|---|---|---|---|---|---|---|---|---|
| Vehicle (PO QD) | Mean | 106 | 180 | 297 | 388 | 535 | 763 | 801 |
| | SEM | 15 | 31 | 48 | 58 | 66 | 69 | 71 |
| MRTX1719 (100 mg/kg PO QD) | Mean | 105 | 165 | 207 | 221 | 214 | 230 | 221 |
| | SEM | 13 | 27 | 38 | 43 | 37 | 50 | 55 |
| Palbociclib (130 mg/kg PO QD) | Mean | 106 | 158 | 236 | 264 | 330 | 434 | 474 |
| | SEM | 13 | 19 | 36 | 34 | 27 | 52 | 64 |
| MRTX1719 (100 mg/kg PO QD) + Palbociclib (130 mg/kg PO QD) | Mean | 105 | 155 | 190 | 178 | 199 | 187 | 182 |
| | SEM | 13 | 18 | 20 | 17 | 25 | 17 | 26 |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method for treating cancer in a subject, the method comprising:
   administering to the subject a therapeutically effective amount of palbociclib and a therapeutically effective amount of a compound of the formula

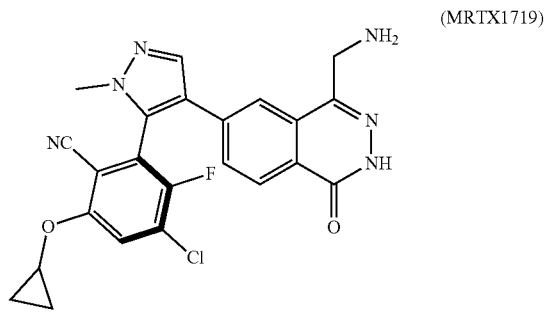

(MRTX1719)

or a pharmaceutically acceptable salt thereof.

2. The method of claim 1, wherein the cancer comprises methylthioadenosine phosphorylase (MTAP) gene homozygous deletion.

3. The method of claim 1, wherein the cancer comprises a cyclin-dependent kinase inhibitor 2A (CDKN2A) gene homozygous deletion.

4. The method of claim 2, wherein the cancer further comprises a Kirsten rat sarcoma viral oncogene homolog glycine-to-cysteine ($KRAS^{G12C}$) gene mutation.

5. The method of claim 1, wherein the cancer is lung cancer, pancreatic cancer, head and neck cancer, bladder cancer, esophageal cancer, lymphoma, stomach cancer, skin cancer, breast cancer, brain cancer, liver cancer, and colon cancer.

6. The method of claim 1, wherein the cancer is lung cancer, pancreatic cancer, head and neck cancer, bladder cancer, esophageal cancer, lymphoma, stomach cancer, melanoma, breast cancer, and brain cancer.

7. The method of claim 1, wherein the cancer is lung cancer.

8. The method of claim 1, wherein the MRTX1719 is a methylthioadenosine (MTA)-cooperative PRMT5 inhibitor.

9. The method of claim 1, wherein the therapeutically effective amount of the MRTX1719 is in the range of about 0.01 to 300 mg/kg per day.

10. The method of claim 1, wherein the therapeutically effective amount of the MRTX1719 is in the range of about 0.1 to 100 mg/kg per day.

11. The method of claim 1, wherein the therapeutically effective amount of the palbociclib is in the range of about 0.01 to 300 mg/kg per day.

12. The method of claim 1, wherein the therapeutically effective amount of the palbociclib is in the range of about 0.1 to 100 mg/kg per day.

13. The method of claim 1, wherein the therapeutically effective amount of the palbociclib is less than 50% of the clinically-established therapeutic amount.

14. The method of claim 1, wherein the palbociclib and the MRTX1719 are administered sequentially.

15. The method of claim 1, wherein the palbociclib and the MRTX1719 are administered simultaneously.

16. The method of claim 1, wherein the subject previously received or completed a first-line chemotherapy.

17. The method of claim 16, wherein the first-line chemotherapy is platinum-and/or taxane-based chemotherapy.

18. The method of claim 1, wherein the cancer is non-small cell lung cancer (NSCLC) or mesothelioma.

* * * * *